United States Patent
Mantell et al.

(10) Patent No.: US 6,900,309 B1
(45) Date of Patent: May 31, 2005

(54) PURINE DERIVATIVES

(75) Inventors: Simon J. Mantell, Sandwich (GB); Sandra M. Monaghan, Sandwich (GB)

(73) Assignee: Pfizer Inc, New York, NY (US)

( * ) Notice: Subject to any disclaimer, the term of this patent is extended or adjusted under 35 U.S.C. 154(b) by 585 days.

(21) Appl. No.: 09/590,585

(22) Filed: Jun. 8, 2000

(30) Foreign Application Priority Data

Jun. 15, 1999 (GB) .............................................. 9913932

(51) Int. Cl.$^7$ .................... C07H 19/167; C07H 19/173; A61K 31/70
(52) U.S. Cl. ................ 536/27.62; 536/27.6; 536/27.63; 536/27.7; 536/26.71; 514/45; 514/46; 514/47
(58) Field of Search .............................. 514/45, 46, 47, 514/825, 861, 865, 866, 925; 536/27.6, 27.61, 27.62, 267, 27.63, 27.7

(56) References Cited

U.S. PATENT DOCUMENTS

| | | | |
|---|---|---|---|
| 6,143,277 A | * 11/2000 | Ashurst et al. ................ | 424/45 |
| 6,232,297 B1 | 5/2001 | Linden et al. ................. | 514/46 |
| 6,372,740 B1 | 4/2002 | Murata et al. ........... | 514/234.2 |
| 6,525,032 B2 | * 2/2003 | Mantell et al. ................ | 514/45 |
| 6,531,457 B2 | 3/2003 | Linden et al. ................. | 514/46 |
| 2003/0162742 A1 | 8/2003 | Linden et al. ................. | 514/45 |

FOREIGN PATENT DOCUMENTS

| | | | |
|---|---|---|---|
| EP | 601322 A2 | 6/1994 | .......... A61K/31/70 |
| EP | 601322 A3 | 6/1994 | .......... A61K/31/70 |
| JP | 5536419 | 9/1978 | .......... C07H/19/16 |
| JP | 55-153789 | * 11/1980 | |
| JP | 03-013934 | * 1/1991 | |
| JP | 07-104426 | * 4/1995 | |
| RU | 2000117278 | 11/1998 | |
| RU | 2001124348 | 7/2003 | |
| WO | 9111172 | 8/1991 | |
| WO | 9402518 | 2/1994 | |
| WO | WO 9414832 | 7/1994 | .......... C07H/19/16 |
| WO | 9855148 | 12/1998 | |

OTHER PUBLICATIONS

Jacobson, Kenneth A. et al., "Adenosine Receptors: Pharmacology, Structure–Activity Relationships, and Therapeutic Potential," Journal of Medicinal Chemistry, 1992, 35 (3), 407–422.*

Matsuda et al., "Synthesis of 2– and 8–Cyanoadenosines and Their Derivatives (Nucleosides and Nucleotides. XXVII)," Chemical & Pharmaceutical Bulletin (Japan), 27(1), 183–192 (1979).*

Berge, et al., J. Pharm. Sci., 66, pp. 1–19 (Jan., 1977, Issue No. 1).

Chem. Pharm. Bull., 28(1), pp. 115–119 (1980).

J. Med. Chem., 35, p. 241–252 (1992).

J. Org. Chem., 62(20), pp. 6833–6841 (1997).

Bioorg. Med. Chem. Lett., 8, pp. 695–698 (1998).

Chem.Abs., 72:55805, XP–002170998 (Acta. Chim. (Budapest), 63(1), pp. 53–58 (1970)).

Chem. Abs., 74:41709, XP–002162656 (Magy. Kem. Foly. (1970), 76(11) pp. 595–597).

Chem.Abs., 122:154099, XP–002162655 (ACS Symp. Ser., (1995), 584 (Synthesis and Chemistry of agrochemicals IV), pp. 206–219).

Nucleosides & Nucleotides, 17(12), pp. 2323–2333 (1998).

* cited by examiner

Primary Examiner—James O. Wilson
Assistant Examiner—Traviss C. McIntosh, III
(74) Attorney, Agent, or Firm—Peter C. Richardson; Gregg C. Benson; William F. Mulholland

(57) ABSTRACT

The present invention relates to compounds of the formula

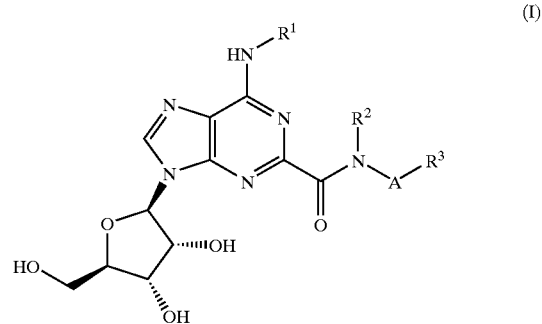

and pharmaceutically acceptable salts and solvates thereof, and to processes for the preparation of, intermediates used in the preparation of, compositions containing and the uses of, such compounds as adenosine A2a receptor agonists.

19 Claims, No Drawings

PURINE DERIVATIVES

REFERENCE TO COPENDING APPLICATIONS

This application claims the benefit under 35 U.S.C. §119 (a–d) of copending Great Britain Application Serial No. 9913932.1, filed Jun. 15, 1999.

This invention relates to purine derivatives. More particularly, this invention relates to 9-(tetrahydro-2-furanyl)-9H-purine-2-carboxamide derivatives and to processes for the preparation of, intermediates used in the preparation of, compositions containing and the uses of, such derivatives.

These derivatives are selective, functional agonists of the human adenosine A2a receptor and may be used as anti-inflammatory agents in the treatment of, inter alia, diseases of the respiratory tract.

Adenosine is a ubiquitous molecule having a central role in mammalian intermediary metabolism. Independently, adenosine acts on multiple surface receptors to produce a variety of responses. Adenosine receptor classification has revealed the presence of at least four subtypes: A1, A2a, A2b and A3. Stimulation of adenosine A2 receptors on the surface of human neutrophils has been reported to potently inhibit a range of neutrophil functions. Activated neutrophils can damage lung tissue by release of reactive oxygen species, for example, superoxide anion radicals ($O_2$'), and granule products, for example, human neutrophil elastase (HNE), amongst other inflammatory mediators. In addition, activated neutrophils perform both de novo synthesis and release of arachidonate products such as leukotriene $B_4$ ($LTB_4$). $LTB_4$ is a potent chemo-attractant that recruits additional neutrophils to the inflammatory focus, whereas released $O_2$ and HNE adversely affect the pulmonary extra-cellular matrix. The A2 receptor subtype mediating many of these responses (02 and $LTB_4$,HNE release and cell adhesion) is established as A2a. The A2 subtype (A2a or A2b) mediating the other effects remains to be established.

Selective agonist activity at the A2a receptor is considered to offer greater therapeutic benefit than the use of non-selective adenosine receptor agonists because interaction with other subtypes is associated with detrimental effects in the lung in animal models and human tissue studies. For example, asthmatics, but not non-asthmatics, bronchoconstrict when challenged with inhaled adenosine. This response is at least in part due to the activation of the A1 receptor subtype. Activation of A1 receptors also promotes neutrophil chemotaxis and adherence to endothelial cells, thus promoting lung injury. Furthermore, many patients with respiratory disease will be co-prescribed $β_2$-agonists, and negative interaction has been shown in animal studies between isoprenaline and adenosine receptors negatively coupled to adenylate cyclase. Degranulation of human mast cells is promoted by activation of adenosine A2b receptors, thus selectivity over the A2b receptor is also advantageous.

We have now surprisingly found the present purine derivatives inhibit neutrophil function and are selective agonists of the adenosine A2a receptor. They may also have antagonist activity at the adenosine A3 receptor. The present compounds may be used to treat any disease for which an adenosine A2a receptor agonist is indicated. They can be used to treat a disease where leukocyte (e.g. neutrophil, eosinophil, basophil, lymphocyte, macrophage)-induced tissue damage is implicated. They are useful as anti-inflammatory agents in the treatment of diseases of the respiratory tract such as adult respiratory distress syndrome (ARDS), bronchitis, chronic bronchitis, chronic obstructive pulmonary disease, cystic fibrosis, asthma, emphysema, bronchiectasis, chronic sinusitis and rhinitis. The present compounds may also be used in the treatment of septic shock, male erectile dysfunction, hypertension, stroke, epilepsy, cerebral ischaemia, peripheral vascular disease, post-ischaemic reperfusion injury, diabetes, rheumatoid arthritis, multiple sclerosis, psoriasis, dermatitis, allergic dermatitis, eczema, ulcerative colitis, Crohns disease, inflammatory bowel disease, *Heliobacter pylofi* gastritis, non-*Heliobacter pylori* gastritis, non-steroidal anti-inflammatory drug-induced damage to the gastro-intestinal tract or a psychotic disorder, or for wound healing.

Accordingly, the present invention provides a compound of the formula:

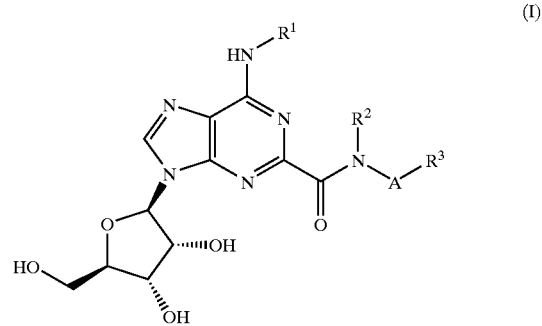

(I)

or a pharmaceutically acceptable salt or solvate thereof, wherein $R^1$ is hydrogen or $C_1$–$C_6$ alkyl optionally substituted by 1 or 2 substituents each independently selected from phenyl and naphthyl, said phenyl and naphthyl being optionally substituted by $C_1$–$C_6$ alkyl, $C_1$–$C_6$ alkoxy, halo or cyano;

$R^2$ is H or $C_1$–$C_6$ alkyl;

A is $C_1$–$C_6$ alkylene;

$R^3$ is (i) hydrogen, $C_1$–$C_6$ alkyl, —$COOR^4$, —CN, —$CONR^4R^4$, $C_3$–$C_8$ cycloalkyl, phenyl or naphthyl, said $C_3$–$C_8$ cycloalkyl, phenyl and naphthyl being optionally substituted by $C_1$–$C_6$ alkyl, phenyl, $C_1$–$C_6$ alkoxy($C_1$–$C_6$) alkyl, $R^4R^4N(C_1$–$C_6)$alkyl, halo($C_1$–$C_6$)alkyl, fluoro ($C_1$–$C_6$) alkoxy, $C_2$–$C_5$ alkanoyl, halo, —$OR^4$, cyano, —$COOR^4$, $C_3$–$C_8$ cycloalkyl, —$S(O)_mR^5$, —$NR^4R$, —$SO_2NR^4R^4$, —$CONR^4R^4$, —$NR^4COR^5$ or —$NR^4SO_2R^5$, or (ii) when A is $C_2$–$C_6$alkylene, —$NR^4R^4$, —$OR^4$, —$OCOR^5$, —$SO_2R^5$, —$SO_2NR^4R^4$ or —$NR^4COR^5$, or (iii) a C-linked, 4- to 11-membered ring, mono- or bicyclic, heterocycle having either from 1 to 4 ring nitrogen atom(s), or 1 or 2 nitrogen and 1 oxygen or 1 sulphur ring atoms, being optionally C-substituted by oxo, $C_1$–$C_6$ alkoxy($C_1$–$C_6$)alkyl, $R^6R^6N(C_1$–$C_6)$alkyl, halo($C_1$–$C_6$)alkyl, fluoro($C_1$–$C_6$)alkoxy, fluoro($C_2$–$C_5$) alkanoyl, halo, cyano, —$OR^6$, $R^7$, $COR^6$, —$NR^6R^6$, —$COOR^6$, —$S(O)_mR^7$, —$SO_2NR^6R^6$, —$CONR^6R^6$, —$NR^6SO_2R^7$ or —$NR^6COR^7$ and optionally N-substituted by $C_1$–$C_6$ alkoxy($C_1$–$C_6$)alkyl, $R^6R^6N$ ($C_2$–$C_6$)alkyl, halo($C_1$–$C_6$)alkyl, fluoro($C_2$–$C_5$)alkanoyl, $R^7$, —$COR^6$, —$COOR^7$, —$SO_2R^7$, —$SO_2NR^6R^6$ or —$CONR^6R^8$, or (iv) when A is $C_2$–$C_6$ alkylene, N-linked azetidinyl, pyrrolidinyl, piperidinyl, piperazinyl, homopiperazinyl or morpholinyl, each being optionally C-substituted by $C_1$–$C_6$ alkyl, phenyl, $C_1$–$C_6$ alkoxy($C_1$—$_6$)alkyl, $R^4R^4N$ ($C_1$–$C_6$)alkyl, halo($C_1$–$C_6$)alkyl, fluoro($C_1$–$C_6$)alkoxy, $C_2$–$C_5$ alkanoyl, halo, —$OR^4$, cyano, —$COOR^4$, $C_3$–$C_6$ cycloalkyl, —$S(O)_mR^5$, —$NR^4R^4$, —$SO_2NR^4R^4$, —$CONR^4R^4$, —$NR^4COR^5$ or —$NR^4SO_2R^5$, and said piperazinyl and homopiperazinyl being optionally N-substituted by $C_1$–$C_6$ alkyl, phenyl, $C_1$–$C_6$ alkoxy ($C_2$–$C_6$)alkyl, $R^4R^4N(C_2$–$C_6)$alkyl, fluoro($C_1$–$C_8$)alkyl, $C_2$-$C_5$ alkanoyl, —$COOR^5$, $C_3$–$C_6$ cycloalkyl, —$SO_2R^5$, —$SO_2NR^4R^4$ or —$CONR^4R^4$;

$R^4$ is H, $C_1$–$C_6$ alkyl, $C_3C_8$ cycloalkyl or phenyl;
$R^5$ is $C_1$–$C_6$ alkyl, $C_3$–$C_8$ cycloalkyl or phenyl;
$R^6$ is H, $C_1$–$C_6$ alkyl, $C_3$–$C_6$ cycloalkyl, phenyl, naphthyl or het;
$R^7$ is $C_1$–$C_6$ alkyl, $C_3$–$C_6$ cycloalkyl, phenyl, naphthyl or het;
m is 0, 1 or 2; and
"het", used in the definitions of $R^6$ and $R^7$, means C-linked pyrrolyl, imidazolyl, triazolyl, thienyl, furyl, thiazolyl, oxazolyl, thiadiazolyl, oxadiazolyl, pyridinyl, pyrimidinyl, pyridazinyl, pyrazinyl, indolyl, isoindolyl, quinolinyl, isoquinolinyl, benzimidazolyl, quinazolinyl, phthalazinyl, benzoxazolyl or quinoxalinyl, each being optionally substituted by $C_1$–$C_6$ alkyl, $C_1$–$C_6$ alkoxy, cyano or halo.

In the above definitions, halo means fluoro, chloro, bromo or iodo and alkyl, alkylene, alkanoyl and alkoxy groups containing the requisite number of carbon atoms can be unbranched or branched chain. The heterocycle as defined in $R^3$, part (iii), above may be aromatic or fully or partially saturated. The expression 'C-linked' used in the definitions of $R^3$ and het means that the group is linked to the adjacent atom by a ring carbon. The expression 'N-linked' used in the definition of $R^3$ means that the group is linked to the adjacent atom by a ring nitrogen. Examples of alkyl include methyl, ethyl, n-propyl, i-propyl; n-butyl, i-butyl, sec-butyl and t-butyl. Examples of alkoxy include methoxy, ethoxy, n-propoxy, i-propoxy, n-butoxy, i-butoxy, sec-butoxy and t-butoxy. Examples of alkanoyl include acetyl and propanoyl. Examples of alkylene include methylene, 1,1-ethylene, 1,2-ethylene, 1,3-propylene and 1,2-propylene. Examples of cycloalkyl include cyclopropyl, cyclobutyl, cyclopentyl, cyclohexyl and cycloheptyl.

Preferred heterocycles included within the definition of "heterocycle" for $R^3$ (iii) are pyrrolyl, imidazolyl, triazolyl, thienyl, furyl, thiazolyl, oxazolyl, thiadiazolyl, oxadiazolyl, pyridinyl, pyrimidinyl, pyridazinyl, pyrazinyl, indolyl, isoindolyl, quinolinyl, isoquinolinyl, benzimidazolyl, quinazolinyl, phthalazinyl, benzoxazolyl and quinoxalinyl, together with partially or fully saturated versions thereof such as azetidinyl, pyrrolidinyl, piperidinyl, piperazinyl, homopiperazinyl and morpholinyl.

In a second aspect, the present invention provides a compound of the formula (I), or a pharmaceutically acceptable salt or solvate thereof, wherein $R^1$ is hydrogen or $C_1$–$C_6$ alkyl substituted by 1 or 2 substituents each independently selected from phenyl and naphthyl;
$R^2$ is hydrogen or $C_1$–$C_6$ alkyl;
A is $C_1$–$C_6$ alkylene; and
$R^3$ is phenyl, naphthyl, $C_3$–$C_8$ cycloalkyl, azetidinyl, pyrrolidinyl, piperidinyl, amino, —NH($C_1$–$C_6$ alkyl) or —N($C_1$–$C_6$ alkyl)$_2$, said phenyl, naphthyl, $C_3$–$C_8$ cycloalkyl, azetidinyl, pyrrolidinyl and piperidinyl being optionally substituted by one or more substituents each independently selected from $C_1$–$C_6$ alkyl, $C_1$–$C_6$ alkoxy, halo($C_1$–$C_8$)alkyl, halo and cyano:
with the proviso that when $R^3$ is N-linked, optionally substituted-azetidinyl, -pyrrolidinyl or -piperidinyl, or is amino, —NH($C_1$–$C_6$ alkyl) or —N($C_1$–$C_6$ alkyl)$_2$, A is $C_2$–$C_6$ alkylene.

The pharmaceutically acceptable salts of the compounds of the formula (I) include the acid addition and the base salts thereof.

Suitable acid addition salts are formed from acids which form non-toxic salts and examples are the hydrochloride, hydrobromide, hydroiodide, sulphate, bisulphate, nitrate, phosphate, hydrogen phosphate, acetate, maleate, fumarate, lactate, tartrate, citrate, gluconate, succinate, saccharate, benzoate, methanesulphonate, ethanesulphonate, benzenesulphonate, p-toluenesulphonate and pamoate salts.

Suitable base salts are formed from bases which form non-toxic salts and examples are the sodium, potassium, aluminium, calcium, magnesium, zinc and diethanolamine salts.

For a review on suitable salts see Berge et al, J. Pharm. Sci., 66, 1–19, 1977.

The pharmaceutically acceptable solvates of the compounds of the formula (I) include the hydrates thereof.

Also included within the present scope of the compounds of the formula (I) are polymorphs thereof.

A compound of the formula (i) may contain one or more additional asymmetric carbon atoms and therefore exist in two or more stereoisomeric forms. The present invention includes the individual stereoisomers of the compounds of the formula (I) together with mixtures thereof.

Separation of diastereoisomers may be achieved by conventional techniques, e.g. by fractional crystallisation, chromatography or H.P.L.C. of a stereoisomeric mixture of a compound of the formula (I) or a suitable salt or derivative thereof. An individual enantiomer of a compound of the formula (I) may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base, as appropriate.

Preferably, $R^1$ is $C_1$–$C_6$alkyl optionally substituted by 1 or 2 phenyl substituents.

Preferably, $R^1$ is $C_1$–$C_6$, alkyl substituted by 1 or 2 phenyl substituents.

Preferably, $R^1$ is $C_1$–$C_4$alkyl substituted by 1 or 2 phenyl substituents.

Preferably, $R^1$ is $C_1$–$C_2$alkyl substituted by 1 or 2 phenyl substituents.

Preferably, $R^1$ is phenylethyl or diphenylethyl.

Preferably, $R^1$ is 2,2-diphenylethyl.

Preferably, $R^2$ is H.

Preferably, A is $C_1$–$C_4$ alkylene.

Preferably, A is unbranched $C_1$–$C_4$ alkylene.

Preferably, A is methylene, ethylene or propylene.

Preferably, A is methylene, 1,2-ethylene or 1,3-propylene.

Preferably, A is 1,2-ethylene.

Preferably, $R^3$ is phenyl optionally substituted as previously defined for this definition for a compound of the formula (I).

Preferably, $R^3$ is phenyl.

Preferably, when A is $C_2$–$C_6$ alkylene, $R^3$ is —$NR^4R^4$.

Preferably, when A is $C_2$–$C_6$ alkylene, $R^3$ is —$NR^4R^4$ wherein $R^4$ is $C_1$–$C_6$alkyl.

Preferably, when A is $C_2$–$C_6$, alkylene, $R^3$ is —$N(CH_3)_2$.

Preferably, $R^3$ is a C-linked, 5- to 7-membered ring monocyclic heterocycle having either from 1 to 4 ring nitrogen atom(s) or 1 or 2 nitrogen and 1 oxygen or 1 sulphur ring atoms, optionally substituted as previously defined for this definition for a compound of the formula (I).

Preferably, $R^3$ is a C-linked, 5- or 6-membered ring monocyclic aromatic heterocycle having either from 1 to 4 ring nitrogen atom(s) or 1 or 2 nitrogen and 1 oxygen or 1 sulphur ring atoms, optionally substituted as previously defined for this definition for a compound of the formula (I).

Preferably, $R^3$ is a C-linked, 5- or 6-membered ring monocyclic aromatic heterocycle having from 1 to 4 ring nitrogen atom(s), optionally substituted as previously defined for this definition for a compound of the formula (I).

Preferably, $R^3$ is C-linked pyridinyl optionally substituted by —$OR^6$, $R^7$, $C_1$–$C_6$ alkoxy($C_1$–$C_6$)alkyl, $R^6R^6N(C_1$–$C_6)$ alkyl or —$NR^6R^6$.

Preferably, $R^3$ is 2-pyridinyl.

Preferably, when A is $C_2$–$C_8$ alkylene, $R^3$ is N-linked pyrrolidinyl, piperidinyl or morpholinyl, each being optionally C-substituted as previously defined for this definition for a compound of the formula (I).

Preferably, when A is $C_2$–$C_6$ alkylene, $R^3$ is N-linked pyrrolidinyl, piperidinyl or morpholinyl, each being optionally C-substituted by $C_1$–$C_6$ alkyl or —$OR^4$.

Preferably, when A is $C_2$–$C_6$ alkylene, $R^3$ is pyrrolidin-1-yl, piperidin-1-yl, 4-isopropylpiperidin-1-yl or morpholin-4-yl.

Preferably, when A is $C_2$–$C_6$ alkylene, $R^3$ is piperidin-1-yl.

Preferably, —A—$R^3$ is phenethyl, 2-(dimethylamino)ethyl, 2-pyridinylmethyl, 2-(2-pyridinyl)ethyl, 3-(1-pyrrolidinyl)propyl, 21-piperidinyl)ethyl, 2-(4-isopropyl-1-piperidinyl)ethyl or 2-(4-morpholinyl)ethyl.

Preferably, —A—$R^3$ is 2-(1-piperidinyl)ethyl.

Particularly preferred examples of a compound of the formula (I) are

9-[(2R,3R,4S,5R)-3,4-dihydroxy-5-(hydroxymethyl)tetrahydro-2-furanyl]-6-[(2,2-diphenylethyl)amino]-N-[2-(1-piperidinyl)ethyl]-9H-purine-2-carboxamide;

9-[(2R,3R,4S,5R)-3,4-dihydroxy-5-(hydroxymethyl)tetrahydro-2-furanyl]-6-[(2,2-diphenylethyl)amino]-N-phenethyl-9H-purine-2-carboxamide;

9-[(2R,3R,4S,5R)-3,4-dihydroxy-5-(hydroxymethyl)tetrahydro-2-furanyl]-6-[(2,2-diphenylethyl)amino]-N-[2-(4-isopropyl-1-piperidinyl)ethyl-9H-purine-2-carboxamide;

9-[(2R,3R,4S,5R)-3,4-dihydroxy-5-(hydroxymethyl)tetrahydro-2-furanyl]-6-[(2,2-diphenylethyl)amino]-N-[3-(1-pyrrolidinyl)propyl]-9H-purine-2-carboxamide;

9-[(2R,3R,4S,5R)-3,4 dihydroxy-5-(hydroxymethyl)tetrahydro-2-furanyl]-6-[(2,2-diphenylethyl)amino]-N-[2-(4-morpholinyl)ethyl]-9H-purine-2-carboxamide;

9-[(2R,3R,4S,5R)-3,4-dihydroxy-5-(hydroxymethyl)tetrahydro-2-furanyl]-6-[(2,2-diphenylethyl)amino]-N-(2-pyridinylmethyl)-9H-purine-2-carboxamide;

9-[(2R,3R,5R)-3,4-dihydroxy-5-(hydroxymethyl)tetrahydro-2-furanyl]-6-[(2,2-diphenylethyl)amino]-N-[2-(2-pyridinyl)ethyl]-9H-purine-2-carboxamide; and 9-[(2R,3R,4S,5R)-3,4-dihydroxy-5-(hydroxymethyl)tetrahydro-2-furanyl]-N-[2-(dimethylamino)ethyl]-[(2,2-diphenylethyl)amino]-9H-purine-2-carboxamide:

together with pharmaceutically acceptable salts and solvates thereof.

The compounds of the formula (I) can be prepared using conventional procedures such as by the following illustrative methods in which $R^1$, $R^2$, $R^3$ and A are as previously defined for a compound of the formula (I) unless otherwise stated.

1. All the compounds of the formula (I) can be prepared by aminocarbonylation reaction of a compound of the formula:

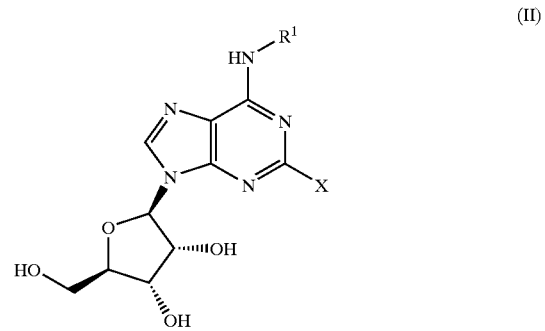

(II)

wherein X is a suitable leaving group such as bromo, iodo, —$Sn(C_1$–$C_{12}$ alkyl$)_3$ or $CF_3SO_2O$—, preferably iodo, with a compound of the formula:

$R^2NH$—A—$R^3$ (III)

in the presence of carbon monoxide and a suitable coupling catalyst. Preferably, the catalyst is a palladium (II) catalyst, more preferably 1,1'-bis(diphenylphosphino)ferrocenedichloropalladium (II) (optionally as a 1:1 complex with dichloromethane). Alternatively, palladium (II) acetate may be used in the presence of a suitable ligand such as 1,1'-bis(diphenylphosphino)ferrocene, triphenylphosphine, tri(o-tolyl)phosphine or (R)-, (S)- or racemic 2,2'-bis(diphenylphosphino)-1,1'-binaphthyl.

In a typical procedure the reaction is carried out in a sealed vessel in the presence of carbon monoxide at an elevated pressure, e.g. about 345 kPa (50 psi), at an elevated temperature, e.g. about 60° C., and in a suitable solvent, e.g. tetrahydrofuran, methanol or ethanol. Optionally, a suitable organic base may be present such as tertiary amine, e.g. triethylamine, N-ethyldiisopropylamine or 4-methylmorpholine.

The intermediates of the formula (II) can be prepared as shown in Scheme 1.

Scheme 1

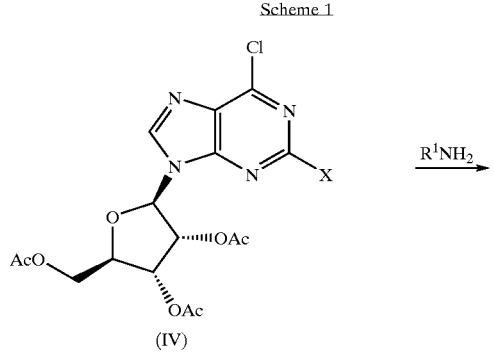

(IV)

-continued

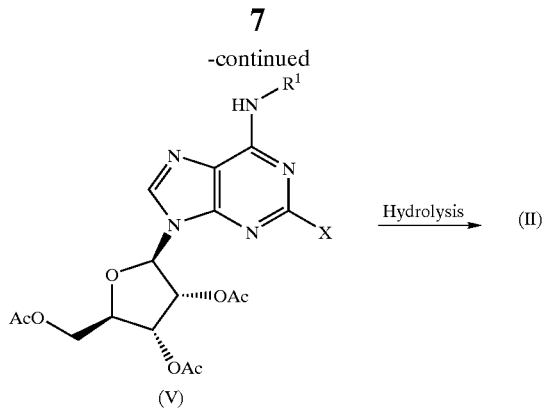

(V)

wherein X is as previously defined for a compound of the formula (II) and "Ac" is acetyl.

In a typical procedure a compound of the formula (IV) is reacted with an amine of the formula $R^1NH_2$ in the presence of a suitable acid acceptor, e.g. triethylamine, and in a suitable solvent, e.g. acetonitrile, at an elevated temperature, if necessary. The product of the formula (V) obtained can be deprotected by hydrolysis to provide a compound of the formula (II) by a conventional procedure such as by using a suitable inorganic base, e.g. sodium carbonate, sodium hydroxide, potassium hydroxide, lithium hydroxide, sodium carbonate, potassium carbonate or caesium carbonate, and in a suitable solvent, e.g. methanol, ethanol, isopropanol, 1,2-dimethoxyethane, tetrahydrofuran, dimethylformamide, acetone, 2-butanone or 4-methyl-2-pentanone, optionally under aqueous conditions, at from 0° C. to the reflux temperature of the solvent, e.g. room temperature. Alternatively, the deprotection can be carried out using a suitable amine base such as triethylamine, diisopropylethylamine, 4-methylmorpholine, ammonia, methylamine, ethylamine or dimethylamine in a suitable solvent such as methanol, ethanol, n-propanol, isopropanol, tetrahydrofuran or dichloromethane at from 0° C. to the reflux temperature of the solvent.

The intermediates of the formula (III) and (IV) are either known compounds or can be prepared by conventional procedures.

2. All the compounds of the formula (I) can be prepared by deprotection of a compound of the formula:

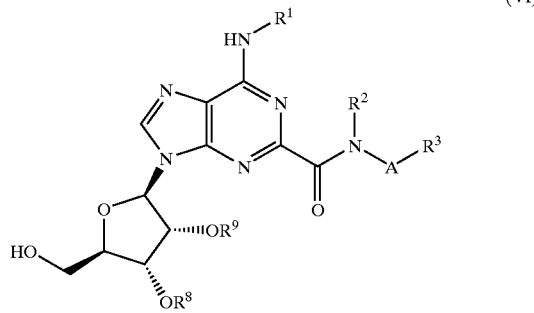

(VI)

wherein $R^8$ and $R^9$ when taken separately are suitable protecting groups such as acetyl or benzoyl or when taken together are a suitable protecting group such as $C_1-C_6$ alkylene, e.g. 1,1-dimethylmethylene.

In a typical procedure, where $R^8$ and $R^9$ taken together are 1,1-dimethylmethylene, a compound of the formula (VI) is treated with a suitable acid such as hydrochloric acid, trifluoroacetic acid, sulphuric acid, p-toluenesulphonic acid, benzenesulphonic acid, methanesulphonic acid, acetic acid or formic acid, or a mixture thereof, optionally in the presence of a suitable solvent, e.g. ethanol, and optionally under aqueous conditions. The reaction may be carried out at an elevated temperature such as at the reflux temperature of the solvent.

The intermediates of the formula (VI) may be prepared as shown in Scheme 2.

Scheme 2

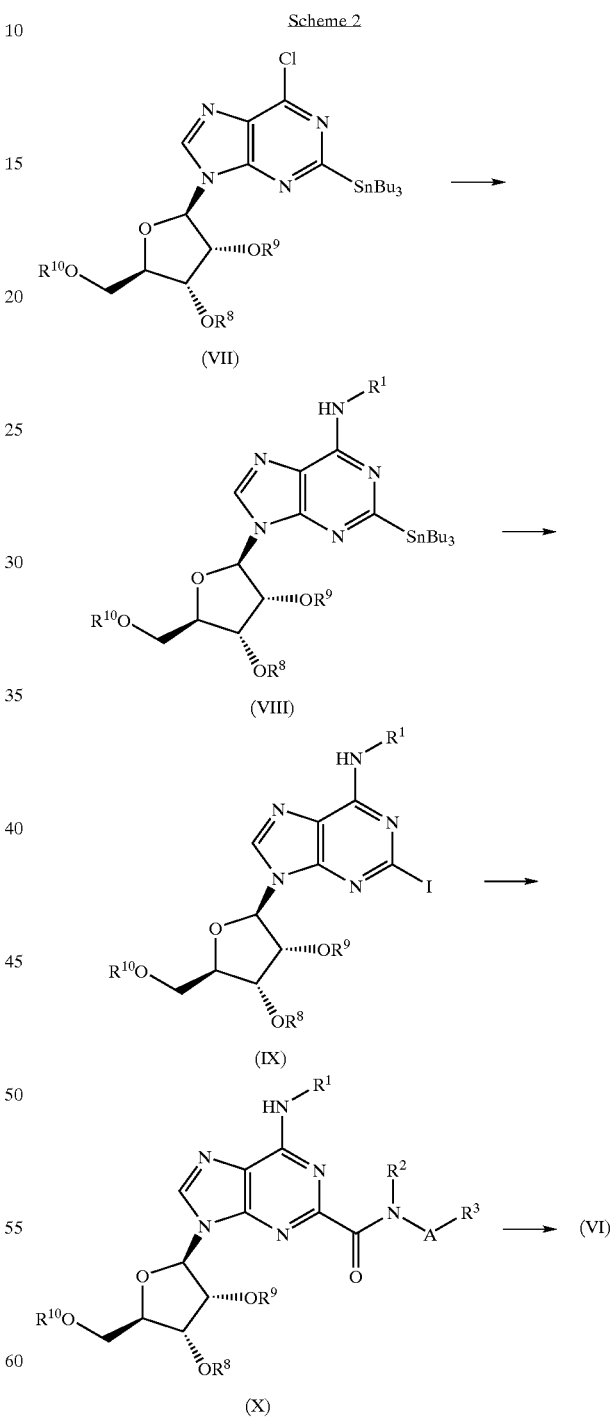

wherein $R^8$ and $R^9$ are as previously defined for a compound of the formula (VI) and $R^{10}$ is suitable protecting group such as trialkylsilyl, e.g. t-butyldimethylsilyl, or t-butyldiphenylsilyl.

In a typical procedure a compound of the formula (VII) (that may be prepared by a conventional procedure, e.g. where $R^8$ and $R^9$ taken together are 1,1-dimethylmethylene and $R^{10}$ is t-butyldimethylsilyl) is treated with a compound of the formula:

$R^1NH_2$      (XI)

in the presence of a suitable solvent, e.g. methanol, ethanol, acetonitrile or isopropanol, optionally in the presence of an additional acid acceptor, e.g. a tertiary amine such as triethylamine, N-ethyldiisopropylamine or 4-methylmorpholine. The reaction is preferably carried out at an elevated temperature such as at the reflux temperature of the solvent.

The compound of the formula (VIII) prepared may be treated with iodine in a suitable solvent such as tetrahydrofuran or dichloromethane at an elevated temperature, e.g. about 50° C., to provide an iodinated compound of the formula (IX).

The compound of the formula (IX) may be converted by aminocarbonylation to an amide of the formula (X) in the presence of an amine of the formula (III) and carbon monoxide under similar conditions to those described in Method 1 for the preparation of a compound of the formula (I) from a compound of the formula (II).

Selective removal of the $R^{10}$ group under suitable deprotection conditions then provides a compound of the formula (VI). Where $R^{10}$ is t-butyldimethylsilyl, the reaction may be carried out using a suitable fluoride source such as tetra-n-butylammonium fluoride or hydrogen fluoride/pyridine, and in a suitable solvent such as acetonitrile or tetrahydrofuran, at room temperature.

3. All the compounds of the formula (I) can be prepared by deprotection of a compound of the formula:

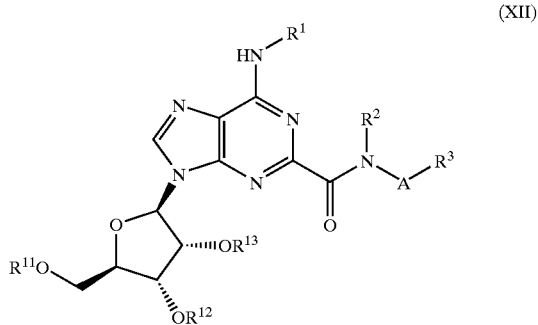

wherein $R^{11}$, $R^{12}$ and $R^{13}$ are suitable protecting groups. Where $R^{11}$, $R^{12}$ and $R^{13}$ are taken separately, examples include acetyl or benzoyl. Alternatively, $R^{12}$ and $R^{13}$ may be taken together and examples include 1,1-dimethylmethylene.

Conventional deprotection conditions may be used and will depend on the nature of the protecting groups to be removed. In a typical procedure where $R^{11}$, $R^{12}$ and $R^{13}$ are each acetyl the deprotection may be achieved using similar conditions to those described for the conversion of a compound of the formula (V) to a compound of the formula (II).

Deprotection of a compound of the formula (XII) to provide a compound of the formula (I) may also be accomplished in situ following the conversion of a compound of the formula (XIII) to a compound of the formula (XII) as described below. Here, where $R^{11}$, $R^{12}$ and $R^{13}$ are each acetyl, the deprotection method using inorganic base is preferred, e.g. the reaction mixture containing a compound of the formula (XII) is treated with aqueous sodium hydroxide solution in 1,2-dimethoxyethane at from 5–20° C.

A compound of the formula (XII) may be prepared as shown in Scheme 3.

Scheme 3

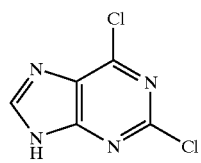

(XIV)

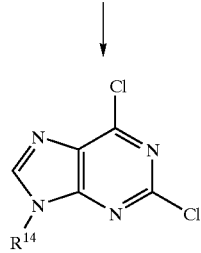

(XV)

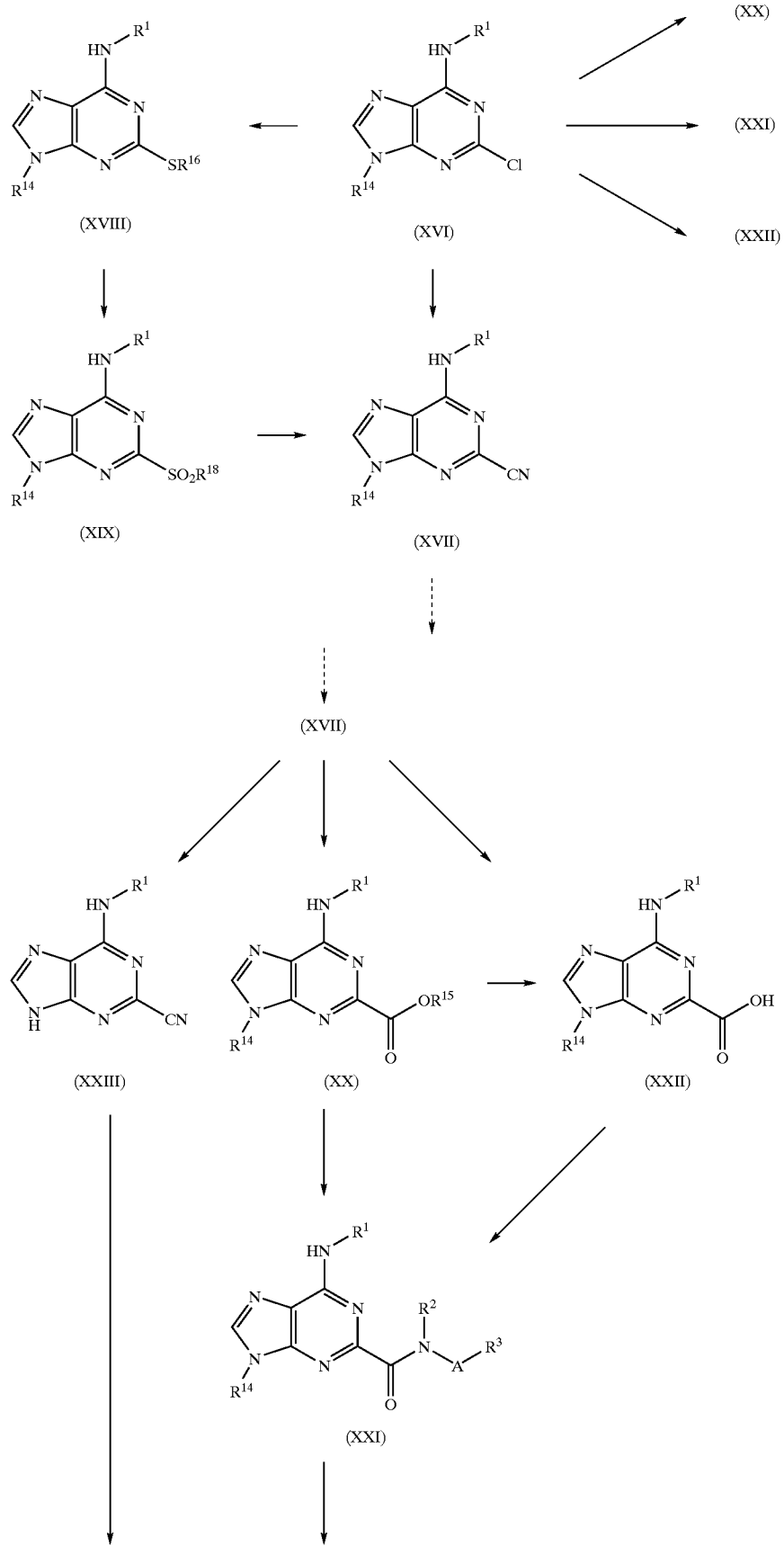

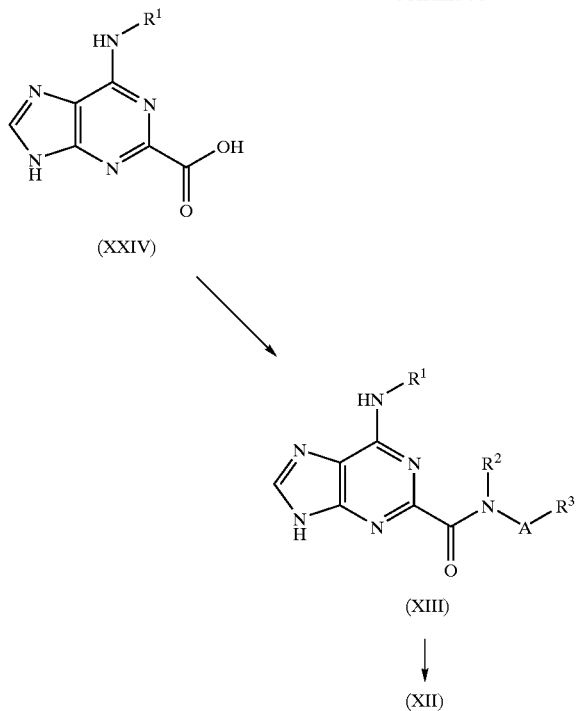

(XXIV)

(XIII)

↓

(XII)

wherein $R^{14}$ is a suitable protecting group, e.g. tetrahydro-2H-pyran-2-yl, and $R^{15}$ and $R^{16}$ are each $C_1$–$C_4$ alkyl, e.g. methyl or ethyl.

A compound of the formula (XIV) may be protected with a suitable protecting group $R^{14}$ under conventional conditions. For example, where $R^{14}$ is tetrahydro-2H-pyran-2-yl this may be obtained by reaction of a compound of the formula (XIV) with 2,3-dihydropyran in a suitable solvent such as ethyl acetate, toluene, dichloromethane, dimethylformamide, tert-butyl methyl ether, diisopropyl ether, tetrahydrofuran or acetonitrile, in the presence of a suitable acid catalyst such as p-toluenesulphonic acid, benzenesulphonic acid, camphorsulphonic acid, hydrochloric acid, sulphuric acid, methanesulphonic acid or pyridinium p-toluenesulfonate, at from 0° C. to the reflux temperature of the solvent. Preferably, the reaction is carried out in ethyl acetate using P-toluenesulphonic acid.

Treatment of a compound of the formula (XV) with a compound of the formula $$R^1NH_2 \quad (XI)$$

in a suitable solvent such as methanol, ethanol or isopropanol, and in the presence of a suitable acid acceptor such as a tertiary amine, e.g. triethylamine, N-ethyldiisopropylamine or 4-methylmorpholine, at up to the reflux temperature of the solvent provides a compound of the formula (XVI).

A compound of the formula (XVI) may be converted to a thioether of the formula (XVIII) by treatment with a sodium or potassium $C_1$–$C_4$ thioalkoxide in a suitable solvent such as dimethylsulphoxide, dimethylformamide or N-methylpyrrolidin-2-one, preferably at an elevated temperature, e.g. 100° C.

Oxidation of a thioether of the formula (XVIII) may be achieved using a suitable oxidant such as Oxone (trade mark) (potassium peroxymonosulphate), dimethyl dioxirane, m-chloroperbenzoic acid or peracetic acid, in a suitable solvent such as water, acetone or dichloromethane, or a mixture thereof, optionally in the presence of a base such as sodium bicarbonate. The sulphone of the formula (XIX) prepared may be treated with a suitable cyanide source such as potassium cyanide, zinc cyanide, sodium cyanide or copper cyanide, in a suitable solvent such as dimethylsulphoxide, dimethylformamide, N-methylpyrrolidin-2-one, tetrahydrofuran or acetonitrile, preferably at an elevated temperature, to provide a nitrile of the formula (XVII).

Direct conversion of a compound of the formula (XVI) to a nitrile of the formula (XVII) may be accomplished by treatment with a suitable cyanide source such as potassium cyanide, zinc cyanide, sodium cyanide or copper cyanide, in a suitable solvent such as dimethylsulphoxide, dimethylformamide, N-methylpyrrolidin-2-one, tetrahydrofuran or acetonitrile, in the presence of a suitable palladium catalyst such as tetrakis(triphenylphosphine)palladium(0) or palladium (II) acetate in association with a suitable ligand such as triphenylphosphine, tri-o-tolylphosphine, 1,1'-bis(diphenylphosphino)ferrocene or (R)-, (S)- or racemic 2,2'-bis(diphenylphosphino)-1,1'-binaphthyl, and in the presence of a suitable base such as a tertiary amine, e.g. triethylamine, N-ethyldiisopropylamine or 4-methylmorpholine. The reaction may be carried out at up to the reflux temperature of the solvent and optionally under an inert gas pressure, e.g. argon. The reaction may also be carried out using a suitable cyanide source such as sodium or potassium cyanide in a suitable solvent such as dimethylsulphoxide, dimethylformamide or N-methylpyrrolidin-2-one, at a temperature of from 20 to 120° C.

A compound of the formula (XVII) may be deprotected to provide a compound of the formula (XXIII) using conventional conditions dependant on the protecting group to be removed. Where $R^{14}$ is tetrahydro-2H-pyran-2-yl, deprotection may be achieved under acidic conditions such as by using a suitable acid, e.g. hydrochloric acid, trifluoroacetic acid, sulphuric acid, trichloroacetic acid, phosphoric acid, p-toluenesulphonic acid, benzenesulphonic acid, methanesulphonic acid or camphorsulphonic acid, and preferably in an alcoholic solvent, e.g. ethanol or isopropanol, that may optionally contain water, typically at from room temperature to the reflux temperature of the solvent.

A nitrile of the formula (XXIII) may be hydrolysed to an acid of the formula (XXIV) under basic conditions such as by using an inorganic base, e.g. lithium hydroxide, sodium hydroxide or potassium hydroxide, in an aqueous $C_1$–$C_4$ alcohol solvent such as methanol, ethanol, isopropanol or industrial methylated spirits.

An acid of the formula (XXIV) may be converted to an amide of the formula (XIII) using conventional peptide coupling conditions, e.g. by activating the acid using a suitable reagent, optionally in the presence of a catalyst, and then by treatment of the activated intermediate with an amine of the formula (III) in a suitable solvent. Suitable activating agents include N,N'-carbonyldiimidazole, thionyl chloride, oxalyl chloride or phosphorus oxychloride and suitable solvents include tetrahydrofuran, dimethylformamide, ethyl acetate, acetonitrile, toluene, acetone or dichloromethane. Alternatively, the acid may be activated by treatment with 1-(3-dimethylaminopropyl)-3-ethylcarbodiimide hydrochloride or dicyclohexylcarbodiimide and 1-hydroxy-7-azabenzotriazole or 1-hydroxybenzotriazole hydrate and then treated with the amine of the formula (III) in the presence of an acid acceptor such as 4-methylmorpholine, triethylamine or N-ethyldiisopropylamine in a solvent such as tetrahydrofuran, dimethylformamide, ethyl acetate, acetonitrile, toluene, acetone or dichloromethane, to provide an amide of the formula (XIII). Alternatively, the acid may be treated with benzotriazol-1-yloxytris(pyrrolidino) phosphonium hexafluorophosphate, bromo-tris-pyrrolidinophosphonium hexafluorophosphate or 2-chloro-1-methylpyridinium iodide and the amine of the formula (III) in the presence of an acid acceptor such as 4-methylmorpholine, triethylamine or N-ethyldiisopropylamine in a solvent such as tetrahydrofuran, dimethylformamide, ethyl acetate or dichloromethane, to provide to an amide of the formula (XIII).

A compound of the formula (XIII) may be converted to a compound of the formula (XII) by reaction with a compound of the formula:

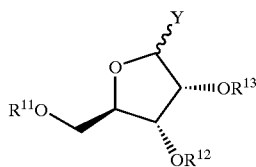

(XXVIII)

wherein Y is a suitable leaving group such as acetoxy, benzoyloxy, methoxy or halo, e.g. chloro, and $R^{11}$, $R^{12}$ and $R^{13}$ are suitable protecting groups as previously defined for a compound of the formula (XII), in the presence of a suitable acid or Lewis acid, e.g. trimethylsilyl trifluoromethanesulphonate. The reaction can be performed using a compound of the formula (XXVIII) in the form of a 2R- or 2S- diastereoisomer, or as an epimeric mixture thereof. The reaction is typically carried out in a suitable solvent, e.g. 1,2-dimethoxyethane, dichloromethane, acetonitrile, 1,1,1-trichloroethane or toluene, or a mixture thereof, preferably by pre-treating the compound of the formula (XIII) in situ with a suitable silylating agent, e.g. trimethylsilyl trifluoromethanesulphonate, N,O-bis(trimethylsilyl) acetamide, trimethylsilyl chloride or hexamethyldisilazane, before adding a compound of the formula (XXVIII). Elevated temperatures may be used in the reaction.

A compound of the formula (XXVIII) can be prepared by conventional procedures.

A nitrile of the formula (XVII) may be converted to an ester of the formula (XX) by treatment with a catalytic or excess amount of an appropriate sodium or potassium $C_1$–$C_4$ alkoxide such as sodium or potassium methoxide or ethoxide, in a corresponding $C_1$–$C_4$ alcohol solvent such as methanol or ethanol, followed by treatment with a suitable acid such as aqueous hydrochloric acid.

The ester of the formula (XX) may be converted to an amide of the formula (XXI) by treatment with an amine of the formula (III), optionally in a suitable solvent such as 1,2-dimethoxyethane or 2-methoxyethyl ether. The reaction may be carried out at elevated temperature and pressure.

An amide of the formula (XXI) may be converted to a compound of the formula (XIII) under conventional deprotection conditions dependant on the protecting group to be removed. Where $R^{14}$ is tetrahydro-2H-pyran-2-yl, this may be achieved under acidic conditions in a suitable solvent, typically using an acid such as hydrochloric acid, trifluoroacetic acid, sulphuric acid, trichloroacetic acid, phosphoric acid, p-toluenesulphonic acid, benzenesulphonic acid, methanesulphonic acid or camphorsulphonic acid, in an alcohol solvent, e.g. isopropanol, that may optionally also contain water. Elevated temperatures may be used in the reaction.

A compound of the formula (XVII) may be converted to an acid of the formula (XXII) under basic conditions, e.g. using an inorganic base such as lithium hydroxide, sodium hydroxide or potassium hydroxide, in an aqueous $C_1$–$C_4$ alcohol solvent such as methanol, ethanol, isopropanol or industrial methylated spirits. The reaction is preferably carried out at an elevated temperature.

An acid of the formula (XXII) may be converted to an amide of the formula (XXI) under similar conditions to those used for the conversion of a compound of the formula (XXIV) to a compound of the formula (XIII).

An ester of the formula (XX) may be converted to an acid of the formula (XXII) under basic conditions, e.g. using an inorganic base such as lithium hydroxide, sodium hydroxide or potassium hydroxide, in an aqueous solvent containing ethanol, methanol, isopropanol, butanol, industrial methylated spirits, tetrahydrofuran, dimethylformamide or 1,2-dimethoxyethane, optionally at an elevated temperature.

A compound of the formula (XVI) may be converted to an ester of the formula (XX) by alkoxycarbonylation using carbon monoxide, a $C_1$–$C_4$ alcohol, a suitable palladium catalyst, optionally a further suitable solvent, and a suitable base such as a tertiary amine. In a typical reaction a catalytic quantity of palladium (II) acetate together with a suitable ligand such as 1,1'-bis(diphenylphosphino)ferrocene, triphenylphosphine, tri-o-tolylphosphine or (R)-, (S)- or racemic 2,2'-bis(diphenylphosphino)-1,1'-binaphthyl, a suitable $C_1$–$C_4$ alcohol such as methanol, ethanol, 1-propanol, isopropanol or 1-butanol, and a tertiary amine base such as triethylamine, N-ethyldiisopropylamine or 4-methylmorpholine, are used under carbon monoxide at an elevated temperature and pressure.

A compound of the formula (XVI) may be converted to an acid of the formula (XXII) by hydroxycarbonylation using carbon monoxide, a suitable palladium catalyst and a suitable base under aqueous conditions. In a typical procedure, a catalytic quantity of palladium (II) acetate together with a suitable ligand such as 1,1'-bis(diphenylphosphino)ferrocene, triphenylphosphine, tri-o-tolylphosphine, or (R)-, (S)- or racemic 2,2'-bis(diphenylphosphino)-1,1'-binaphthyl, a base such as an alkali metal hydroxide, e.g. sodium hydroxide, or a tertiary amine, and water, together with, optionally, a suitable water miscible solvent such as methanol, ethanol, 1-propanol, tetrahydrofuran, 1,2-dimethoxyethane, dimethylformamide or isopropanol, are used under an atmosphere of carbon monoxide at elevated temperature and pressure.

A compound of the formula (XVI) may be converted to a compound of the formula (XXI) by aminocarbonylation using carbon monoxide, an amine of the formula (III), a suitable palladium catalyst and a suitable solvent, optionally in the presence of a suitable base. In a typical procedure, a catalytic quantity of palladium (II) acetate together with a suitable ligand such as 1,1'-bis(diphenylphosphino)ferrocene, triphenylphosphine, tri-o-tolylphosphine or (R)-, (S)- or racemic 2,2'-bis(diphenylphosphino)-1,1'-binaphthyl, a solvent such as tetrahydrofuran, dimethylformamide, 1.2-dimethoxyethane, ethyl acetate, N-methyl-2-pyrrolidinone, t-butyl methyl ether or diisopropyl ether, a tertiary amine base such as triethylamine, N-ethyldiisopropylamine or 4-methylmorpholine, are used under an atmosphere of carbon monoxide at elevated temperature and pressure.

4. All the compounds of the formula (I) can be prepared by reaction of a compound of the formula:

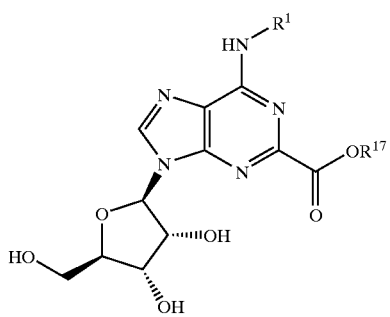

(XXV)

wherein $R^{17}$ is H or a suitable ester-forming group such as $C_1$–$C_4$ alkyl or benzyl, with an amine of the formula (III), and where $R^{17}$ is H in the presence of a suitable peptide coupling agent, under conventional conditions. In a typical procedure, the reagents are heated together, optionally in the presence of a suitable solvent such as 1,2-dimethoxyethane or 2-methoxyethyl ether, at an elevated temperature, e.g. from 60 to 120° C., and optionally under pressure.

A compound of the formula (XXV) may be prepared as shown in Scheme

Scheme 4

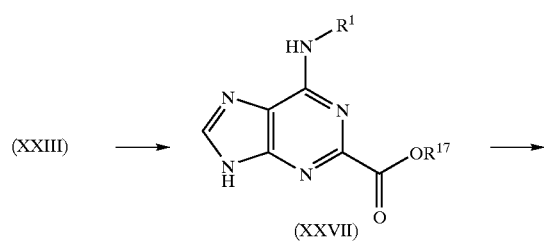

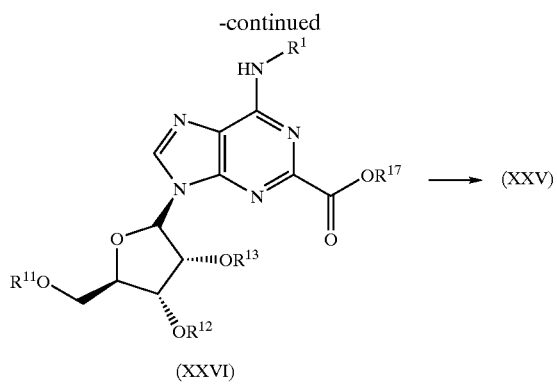

wherein $R^{17}$ is a suitable ester-forming group such as $C_1$–$C_4$ alkyl or benzyl and $R^{11}$, $R^{12}$ and $R^{13}$ are suitable protecting groups as previously defined for a compound of the formula (XXVIII).

In a typical procedure, a nitrile of the formula (XXIII) is converted to an ester of the formula (XXVII) under basic conditions, e.g. using a sodium or potassium $C_1$–$C_4$ alkoxide such as sodium or potassium methoxide or ethoxide, in a corresponding $C_1$–$C_4$ alkanol solvent such as methanol or ethanol, at from room temperature to the reflux temperature of the solvent, followed by treatment with a suitable acid such as aqueous hydrochloric acid.

An ester of the formula (XXVII) may be converted to a compound of the formula (XXVI) by reaction with a compound of the formula (XXVIII) under similar conditions to those used for the conversion of a compound of the formula (XIII) to a compound of the formula (XII).

A compound of the formula (XXVI) may be converted to a compound of the formula (XXV) under similar conditions to those used for the conversion of a compound of the formula (XII) to a compound of the formula (I) such as by using sodium carbonate in methanol where $R^{11}$, $R^{12}$ and $R^{13}$ are each acetyl. An acid of the formula (XXV) ($R^{17}$=H) may be prepared from the corresponding ester by conventional procedures.

All of the above reactions and the preparations of novel starting materials using in the preceding methods are conventional and appropriate reagents and reaction conditions for their performance or preparation as well as procedures for isolating the desired products will be well-known to those skilled in the art with reference to literature precedents and the Examples and Preparations hereto. In particular, suitable protection and deprotection procedures are well-known in the art. e.g. as described in Greene et al, "Protective Groups in Organic Synthesis", Third Edition, John Wiley & Sons Ltd.

A pharmaceutically acceptable salt of a compound of the formula (I) may be readily prepared by mixing together solutions of a compound of the formula (I) and the desired acid or base, as appropriate. The salt may precipitate from solution and be collected by filtration or may be recovered by evaporation of the solvent.

The anti-inflammatory properties of the compounds of the formula (1) are demonstrated by their ability to inhibit neutrophil function which indicates A2a receptor agonist activity. This is evaluated by determining the compound profile in an assay where superoxide production was measured from neutrophils activated by fMLP. Neutrophils were isolated from human peripheral blood using dextran sedimentation followed by centrifugation through Ficoll-Hypaque solution. Any contaminating erythrocytes in the granulocyte pellet were removed by lysis with ice-cold distilled water. Superoxide production from the neutrophils was induced by fMLP in the presence of a priming concentration of cytochalasin B. Adenosine deaminase was included in the assay to remove any endogenously produced adenosine that might suppress superoxide production. The effect of the compound on the fMLP-induced response was monitored colorometrically from the reduction of cytochrome C within the assay buffer. The potency of the compounds was assessed by the concentration giving 50% inhibition ($IC_{50}$) compared to the control response to fMLP.

The compounds of the formula (I) can be administered alone but will generally be administered in admixture with a suitable pharmaceutical excipient, diluent or carrier selected with regard to the intended route of administration and standard pharmaceutical practice.

For example, the compounds of the formula (I) can be administered orally, buccally or sublingually in the form of tablets, capsules, ovules, elixirs, solutions or suspensions, which may contain flavouring or colouring agents, for immediate-, delayed-, sustained-, pulsed- or controlled-release applications.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or a high molecular weight polyethylene glycol. For aqueous suspensions and/or elixirs, the compounds of the formula (I) may be combined with various sweetening or flavouring agents, colouring matter or dyes, with emulsifying and/or suspending agents and with diluents such as water, ethanol, propylene glycol or glycerin, and combinations thereof.

The compounds of the formula (I) can also be administered parenterally, for example, intravenously, intra-arterially, intraperioneally, intrathecally, intraventricularly, intrasternally, intracranially, intramuscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

For oral and parenteral administration to human patients, the daily dosage level of the compounds of the formula (I) will usually be from 0.01 to 100 mg/kg, preferably from 0.1 to 100 mg/kg (in single or divided doses).

Thus tablets or capsules of the compound of the formula (I) may contain from 5 to 500 mg of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

The compounds of formula (I) can also be administered intranasally or by inhalation and are conveniently delivered in the form of a dry powder inhaler or an aerosol spray presentation from a pressurised container, pump, spray, atomiser or nebuliser, with or without the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A [trade mark]) or 1,1,1,2,3,3,3-heptafluoropropane (HFA 227EA [trade mark]), carbon dioxide or other suitable gas. In the case of a pressurised aerosol, the dosage unit may be determined by providing a valve to deliver a metered amount. The pressurised container, pump, spray, atomiser nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insulator may be formulated to contain a powder mix of a compound of the formula (I) and a suitable powder base such as lactose or starch.

Aerosol or dry powder formulations are preferably arranged so that each metered dose or "puff" contains from 20 to 4000 μg of a compound of the formula (I) for delivery to the patient. The overall daily dose with an aerosol will be in the range of from 20 μg to 20 mg which may be administered in a single dose or, more usually, in divided doses throughout the day.

Alternatively, the compounds of the formula (I) can be administered in the form of a suppository or pessary, or they may be applied topically in the form of a lotion, solution, cream, ointment or dusting powder. The compounds of the formula (I) may also be transdermally administered, for example, by the use of a skin patch.

For application topically to the skin, the compounds of the formula (I) can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

The compounds of the formula (I) may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO-A-91/11172, WO-A-94/02518 and WO-A-98/55148.

It is to be appreciated that all references herein to treatment include curative, palliative and prophylactic treatment.
 (i) Thus the invention provides:—
(i) a compound of the formula (I) or a pharmaceutically acceptable salt or solvate thereof, (ii) a process for the preparation of a compound of the formula (I) or a pharmaceutically acceptable salt or solvate thereof;
(iii) a pharmaceutical composition including a compound of the formula (I) or a pharmaceutically acceptable salt or solvate thereof, together with a pharmaceutically acceptable excipient, diluent or carrier;
(iv) a compound of the formula (I) or a pharmaceutically acceptable salt, solvate or composition thereof, for use as a medicament;
(v) the use of a compound of the formula (I) or of a pharmaceutically acceptable salt, solvate or composition thereof, for the manufacture of a medicament having A2a receptor agonist activity;
(vi) the use of a compound of the formula (I) or of a pharmaceutically acceptable salt, solvate or composition thereof, for the manufacture of an anti-inflammatory agent;
(vii) the use of a compound of the formula (I) or of a pharmaceutically acceptable salt, solvate or composition thereof, for the manufacture of a medicament for the treatment of a respiratory disease;
(viii) use as in (vii) where the disease is selected from the group consisting of adult respiratory distress syndrome (ARDS), bronchitis, chronic bronchitis, chronic obstructive pulmonary disease, cystic fibrosis, asthma, emphysema, bronchiectasis, chronic sinusitis and rhinitis;
(ix) the use of a compound of the formula (I) or of a pharmaceutically acceptable salt, solvate or composition thereof, for the manufacture of a medicament for the treatment of septic shock, male erectile dysfunction, hypertension, stroke, epilepsy, cerebral ischaemia, peripheral vascular disease, post-ischaemic reperfusion injury, diabetes, rheumatoid arthritis, multiple sclerosis, psoriasis, dermatitis, allergic dermatitis, eczema, ulcerative colitis, Crohns disease, inflammatory bowel disease, *Heliobacter pylori* gastritis, non-*Heliobacter pylori* gastritis, non-steroidal anti-inflammatory drug-induced damage to the gastrointestinal tract or a psychotic disorder, or for wound healing;
(x) a method of treatment of a mammal, including a human being, with a A2a receptor agonist including treating said mammal with an effective amount of a compound of the formula (I) or with a pharmaceutically acceptable salt, solvate or composition thereof;
(xi) a method of treatment of a mammal, including a human being, to treat an inflammatory disease including treating said mammal with an effective amount of a compound of the formula (I) or with a pharmaceutically acceptable salt, solvate or composition thereof;
(xii) a method of treatment of a mammal, including a human being, to treat a respiratory disease including treating said mammal with an effective amount of a compound of the formula (I) or with a pharmaceutically acceptable salt, solvate or composition thereof;
(xiii) a method as in (xii) where the disease is selected from the group consisting of adult respiratory distress syndrome (ARDS), bronchitis, chronic bronchitis, chronic obstructive pulmonary disease, cystic fibrosis, asthma, emphysema, bronchiectasis, chronic sinusitis and rhinitis;
(xiv) a method of treatment of a mammal, including a human being, to treat septic shock, male erectile dysfunction, hypertension, stroke, epilepsy, cerebral ischaemia, peripheral vascular disease, post-ischaemic reperfusion injury, diabetes, rheumatoid arthritis, multiple sclerosis, psoriasis, dermatitis, allergic dermatitis, eczema, ulcerative colitis, Crohns disease, inflammatory bowel disease, *Heliobacter pylori* gastritis, non-*Heliobacter pylori* gastritis, non-steroidal anti-inflammatory drug-induced damage to the gastrointestinal tract or a psychotic disorder, or for wound healing, including treating said mammal with an effective amount of a compound of the formula (I) or with a pharmaceutically acceptable salt, solvate or composition thereof; and
(xv) certain novel intermediates disclosed herein.

The following Examples illustrates the preparation of the compounds of the formula (I):—

EXAMPLE 1

9-[(2R,3R,4S,5R)-3,4-Dihydroxy-5-(hydroxymethyl) tetrahydro-2-furanyl]-6-[(2,2-diphenylethyl)amino]-N-[2-(1-piperidinyl)ethyl]-9H-purine-2-carboxamide

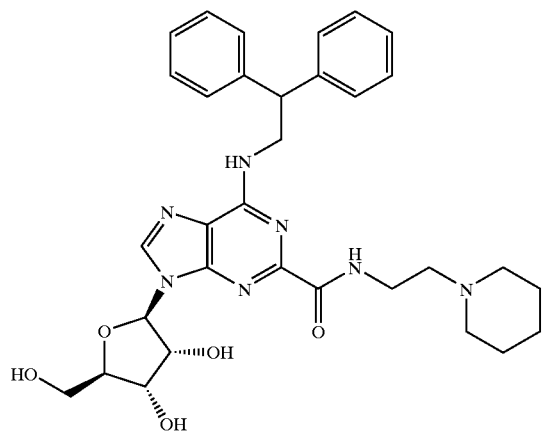

A solution of (2R,3R,4S,5R)-2-{6-[(2,2-diphenylethyl) amino]-2-iodo-9H-purin-9-yl}-5-(hydroxymethyl) tetrahydro-3,4-furandiol (59, 8.7 mmol) (Preparation 2), 1,1'-bis(diphenylphosphino)ferrocenedichloropalladium(II) (1:1 complex with dichloromethane) (0.7 g, 0.9 mmol) and 1-(2-aminoethyl)piperidine (3.49, 26.5 mmol) in anhydrous tetrahydrofuran (250 ml) was heated at 60° C., under a carbon monoxide atmosphere at 345 kPa (50 psi) in a sealed vessel for 24 hours. The mixture was cooled, filtered through a pad of Arbocel (trade mark) and the filtrate diluted with tetrahydrofuran (150 ml) and ethyl acetate (400 ml). The resulting solution was washed with water (3×300 ml) and the organic phase extracted with 2 M aqueous hydrochloric acid solution (50 ml). The acidic aqueous phase was washed with ethyl acetate (20 ml) then the pH adjusted to >7 by addition of 0.88 aqueous ammonia solution. Ethyl acetate (100 ml) was added and the mixture stirred for 10 minutes after which time a white solid formed. This solid was filtered, washed sequentially with water and ethyl acetate and dried at 70° C. under reduced pressure to yield the title compound as a white solid (2.8 g).

$^1$H-NMR (300 MHz, CDCl$_3$) δ: 8.50 (1H, br s), 8.35 (1H, s), 7.35–7.20 (10H, m), 5.95 (1H, d), 5.90 (1H, br s), 4.70–4.60 (2H, m), 4.40–4.30 (3H, m), 4.20 (1H, m), 4.10–4.00 (2H, m), 3.50–3.40 (2H, m), 2.55–2.45 (2H, m), 2.30 (4H, br s), 1.40–1.20 (6H, m).

LRMS (thermospray): m/z [MH$^+$] 602

Analysis: Found C, 63.61; H, 6.51; N, 16.26% C$_{32}$H$_{39}$N$_7$O$_5$ requires C, 63.88; H, 6.53; N, 16.30%

EXAMPLE 2
9-[(2R,3R,4S,5R)-3,4-Dihydroxy-5-(hydroxymethyl) tetrahydro-2-furanyl]-6-(2,2-diphenylethyl)amino]-N-phenethyl-9H-purine-2-carboxamide

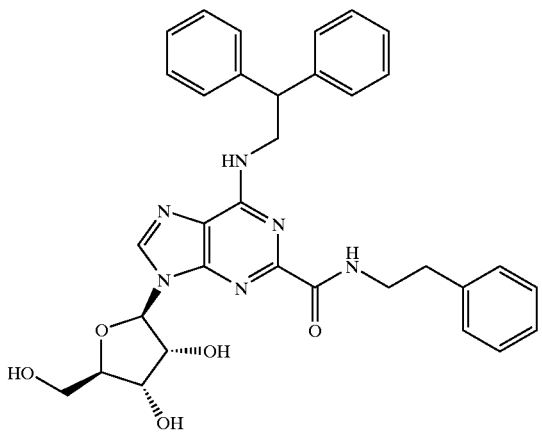

A solution of 9-[(3aR,4R,6R,6aR)$_6$-(hydroxymethyl)-2,2-dimethyltetrahydrofuro[3,4-d][1,3]dioxol-4-yl]-6-[(2,2-diphenylethyl)amino]-N-phenethyl-9H-purine-2-carboxamide (0.589, 0.91 mmol) (Preparation 7) and formic acid (0.5 ml) in a mixture of acetic acid and water (1:1, by volume, 25 ml) was heated under reflux for 1 hour. The mixture was then cooled and basified to pH8 with saturated aqueous sodium hydrogen carbonate solution. The resulting precipitate was filtered off to give the crude product. This solid was purified by column chromatography on silica gel eluting with a solvent system of dichloromethane:methanol:0.88 ammonia (90:10:1.5, by volume) to yield a solid which was triturated with diethyl ether, filtered and dried to afford the title compound as a solid (186 mg).

$^1$H-NMR (300 MHz, CDCl$_3$+DMSO-d$_6$) δ: 7.70–7.92 (2H, m), 6.90–7.21 (15H, m), 6.23 (1H br s), 5.76 (1H, br s), 5.36–5.63 (1H br s), 4.82 (2H, m), 4.18–4.38 (3H, m), 4.14 (1H, s), 3.90–4.13 (2H, br s), 3.82 (1H, d), 3.66 (1H, d), 3.56 (2H, q), 2.76 (2H, t).

LRMS (thermospray): m/z [MH$^+$] 595
Analysis: Found C, 66.11; H, 5.82; N, 14.01%; C$_{33}$H$_{34}$N$_6$O$_5$, 0.25 H$_2$O requires C, 66.16; H, 5.76; N, 14.03%

EXAMPLE 3
9-[(2R,3R,4S,5R)-3,4-Dihydroxy-5-(hydroxymethyl) tetrahydro-2-furanyl]-6-[(2,2-diphenylethyl)amino]-N-[2-(4-isopropyl-1-piperidinyl)ethyl]-9H-purine-2-carboxamide

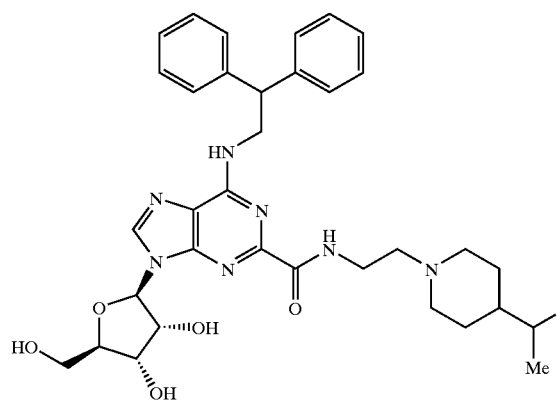

A mixture of methyl 9-[(2R,3R,4S,5R)-3,4-dihydroxy-5-(hydroxymethyl)-tetrahydro-2-furanyl]-6-[(2,2-diphenylethyl)amino]-9H-purine-2-carboxylate (Preparation 18) (92 mg, 0.18 mmol) and 2-(4-isopropyl-1-piperidinyl)ethylamine (Preparation 20) (100 mg, 0.6 mmol) was heated at 120° C. under a nitrogen atmosphere for 75 minutes. The reaction mixture was allowed to cool to room temperature and diethyl ether (2 ml) added to precipitate a crude product. The solvent was decanted off the gum which was then triturated with ethyl acetate (2 ml). The resulting white solid was filtered off and dried to give the title compound (59 mg).

$^1$H-NMR (300 MHz, CD$_3$OD) δ: 8.40 (1H, br s), 7.40–7.10 (10 H, m), 6.05 (1H, d), 4.60 (1H, m), 4.504.30 (4H, m), 4.15 (1H, m); 3.90, 3.80 (2H, AB system), 3.60 (2H, m), 3.00 (2H, m), 2.60 (2H, m), 2.05 (2H, m), 1.65 (2H, m), 1.40–1.20 (3H, m), 1.05 (1H, m), 0.90 (6H, d).

LRMS (thermospray): m/z [MH$^{30}$] 644

EXAMPLE 4

9-[(2R,3R,4S,5R)-3,4-Dihydroxy-5-(hydroxymethyl) tetrahydro-2-furanyl]-6-](2,2-diphenylethyl)amino]-N-[3-(1-pyrrolidinyl)propyl]-9H-purine-2-carboxamide

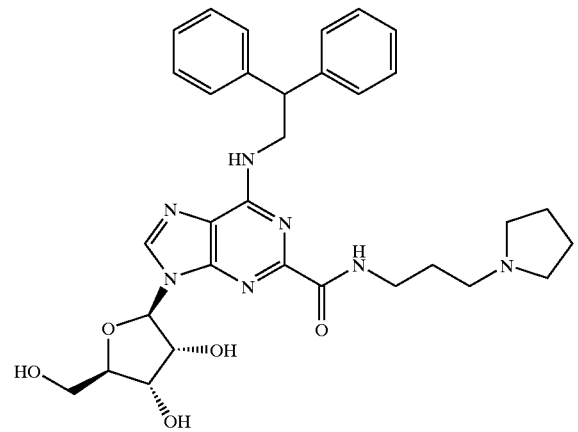

A mixture of methyl 9-[(2R,3R,4S,5R)-3,4-dihydroxy-5-(hydroxymethyl)-tetrahydro-2-furanyl]-6-[(2,2-diphenylethyl)amino]-9H-purine-2-carboxylate (Preparation 18) (92 mg, 0.18 mmol) and N-(3-aminopropyl)pyrrolidine (0.25 ml, 1.95 mmol) was heated at 120° C. under a nitrogen atmosphere for 75 minutes. The reaction mixture was allowed to cool to room temperature and diethyl ether (2 ml) added to precipitate a crude product. The solvent was decanted off the gum which was purified by column chromatography on silica gel eluting with dichloromethane:methanol (80:20, by volume). Trituration with diethyl ether gave the title compound as a white solid (34 mg).

¹H-NMR (300 MHz, CD₃OD) δ: 8.40 (1H, br s), 7.40 7.05 (10H, m), 6.05 (1H, d), 4.60 (1H, m), 4.50 4.30 (4H, m), 4.15 (1H, m); 3.90, 3.80 (2H, AB system), 3.50 (2H, m), 2.60 (6H, m), 1.90–1.80 (6H, m).

LRMS (thermospray): m/z [MH⁺] 602

EXAMPLE 5

9-[(2R,3R,4S,5R)-3,4-Dihydroxy-5-(hydroxymethyl)tetrahydro-2-furanyl]-6-[(2,2-diphenylethyl)amino]-N-[2-(4-morpholinyl)ethyl]-9H-purine-2-carboxamide

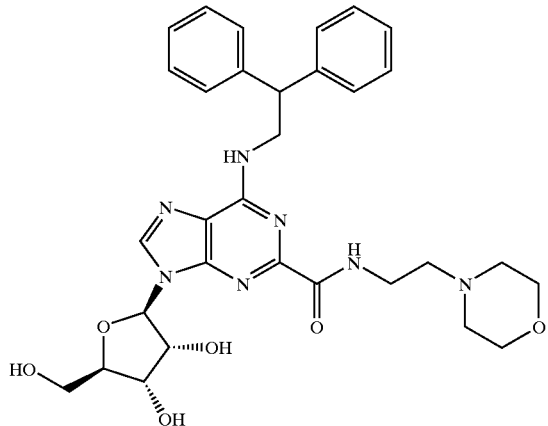

A mixture of methyl 9-[(2R,3R,4S,5R)-3,4-dihydroxy-5-(hydroxymethyl)-tetrahydro-2-furanyl]-6-[(2,2-diphenylethyl)amino]-9H-purine-2-carboxylate (Preparation 18) (92 mg, 0.18 mmol) and N-(2-aminoethyl)morpholine (0.25 ml, 1.9 mmol) were heated at 120° C. under a nitrogen atmosphere for 75 minutes. The reaction mixture was allowed to cool to room temperature and diethyl ether (2 ml) added to precipitate the title compound as a white solid which was filtered off and dried (68 mg).

¹H-NMR (300 MHz, CDCl₃) δ: 8.50 (1H, br s), 8.40 (1H, s), 7.40–7.20 (10H, m), 6.00 (2H, m), 4.65–4.60 (2H, m), 4.40–4.20 (4H, m), 4.15 (2H, m); 3.60–3.40 (6H, m), 2.60–2.50 (3H, m), 2.40–2.35 (4H, m).

LRMS (thermospray): m/z [MH⁺] 604

EXAMPLE 6

9-[(2R,3R,4S. 5R)-3,4-Dihydroxy-5-(hydroxymethyl)tetrahydro-2-furanyl-6-[(2,2-diphenylethyl)amino]-N-(2-pyridinylmethyl)-9H-purine-2-carboxamide

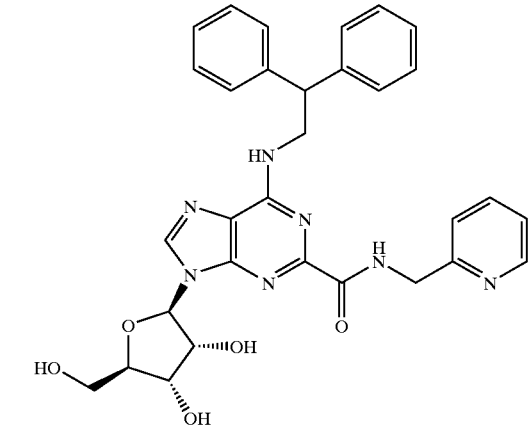

A mixture of methyl 9-[(2R,3R,4S,5R3,4-dihydroxy-5-(hydroxymethyl) tetrahydro-2-furanyl]-6[(2,2-diphenylethyl)amino]-9H-purine-2-carboxylate (Preparation 18) (92 mg, 0.18 mmol) and 2-(aminomethyl)pyridine (0.25 ml, 2.4 mmol) was heated at 120° C. under a nitrogen atmosphere for 75 minutes. The reaction mixture was allowed to cool to room temperature and diethyl ether (2 ml) added to precipitate a crude product. The solvent was decanted from the gum which was then triturated with ethyl acetate (2 ml). The resulting white solid was filtered off and dried to give the title compound (73 mg).

¹H-NMR (300 MHz, d₆-DMSO) δ: 9.15 (1H, m), 8.50–8.40 (2H, m), 8.05 (1H, m), 7.80 (1H, m), 7.40–7.10 (12H, m), 5.95 (1H, d), 5.45 (1H, br s), 5.20 (1H, br s), 5.10 (1H, br s), 4.70–4.50 (4H, m), 4.30 (2H, m), 4.20 (1H, m); 3.95 (1H, m), 3.70–3.50 (2H, m).

LRMS (thermospray): m/z [MH⁺] 582

EXAMPLE 7

9-[(2R,3R,4S,5R)-3,4-Dihydroxy-5-(hydroxymethyl)tetrahydro-2-furanyl]-6-(2,2-diphenylethyl)amino]-N-[2-(2-pyridinyl)ethyl]-9H-purine-2-carboxamide

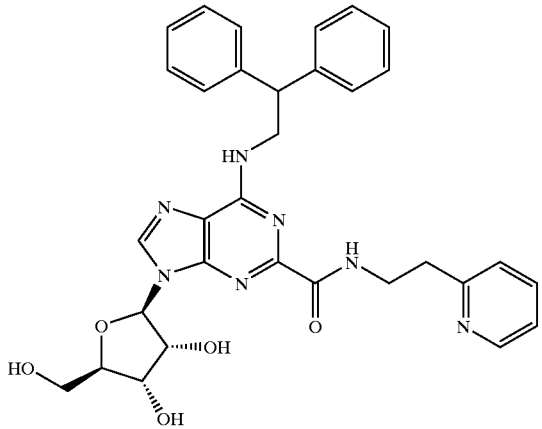

A mixture of methyl 9-[(2R,3R,4S,5R3,4-dihydroxy-5-(hydroxymethyl)-tetrahydro-2-furanyl]-6-[(2,2-diphenylethyl)amino]-9H-purine-2-carboxylate (Preparation 18) (92 mg, 0.18 mmol) and 2-(2-aminoethyl)pyridine (0.25 ml, 2.1 mmol) was heated at 120° C. under a nitrogen atmosphere for 75 minutes. The reaction mixture was allowed to cool to room temperature and diethyl ether (2 ml) added to precipitate a crude product. The solvent was decanted from the gum which was purified by column chromatography on silica gel eluting with dichloromethane:methanol (95:5, by volume). Trituration with diethyl ether gave the title compound as a white solid (49 mg).

$^1$H-NMR (300 MHz, CD$_3$OD) δ: 8.40 (2H, m), 7.70 (1H, m), 7.40–7.10 (12H, m), 6.05 (1H, d), 4.60 (1H, m), 4.45 (1H, m), 4.35 (3H, m), 4.15 (1H, m), 3.95–3.70 (4H, m), 3.10 (2H, m).

LRMS (thermospray): m/z [MH$^+$] 596

EXAMPLE 8

9-[(2R,3R,4S,5R)-3,4-Dihydroxy-5-(hydroxymethyl)tetrahydro-2-furanyl]-N-[2-(dimethylamino)ethyl]-6-[(2,2-diphenylethyl)amino]-9H-purine-2-carboxamide

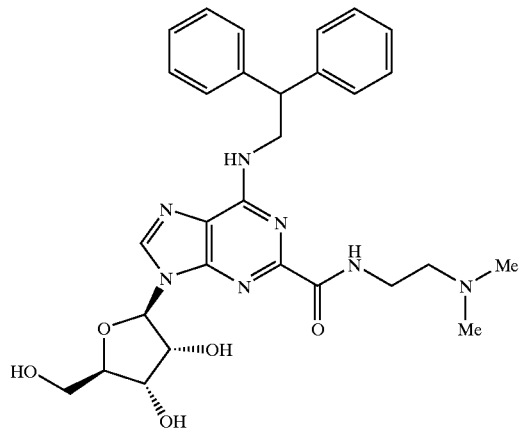

A mixture of methyl 9-[(2R,3R,4S,5R3,4-dihydroxy-5-(hydroxymethyl)-tetrahydro-2-furanyl]4-[(2,2-diphenylethyl)amino]-9H-purine-2-carboxylate (Preparation 18) (92 mg, 0.18 mmol) and N,N-dimethylethylenediamine (0.25 ml, 2.3 mmol) was heated at 120° C. under a nitrogen atmosphere for 75 minutes. The reaction mixture was allowed to cool to room temperature and diethyl ether (2 ml) added to precipitate a crude product. The solvent was decanted off the gum which was purified by column chromatography on silica gel eluting with dichloromethane:methanol:concentrated aqueous ammonia (90:10:1, by volume). Trituration with diethyl ether gave the title compound as a white solid (51 mg).

$^1$H-NMR (400 MHz, CDCl$_3$) δ: 8.50 (1H, br s), 8.20 (1H, s), 7.30–7.15 (10H, m), 6.05 (1H, br s), 5.90 (1H, m), 4.70 (1H, m), 4.60 (1H, m), 4.40–4.30 (3H, m), 4.20 (1H, m); 4.00 (2H, m), 3.40 (2H, m), 2.50 (2H, m), 2.15 (6H, s).

LRMS (thermospray): m/z [MH$^+$] 562

EXAMPLE 9

9-[(2R,3R,4S,5R)-3,4-Dihydroxy-5-(hydroxymethyl)tetrahydro-2-furanyl]-6-[(2,2-diphenylethyl)amino]-N-[2-(1-piperidinyl)ethyl]-9H-purine-2-carboxamide

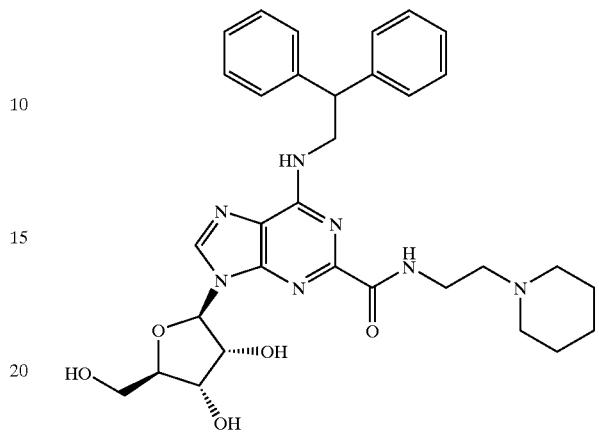

To a stirred solution of 6-[(2,2-diphenylethyl)amino]-N-[2-(1-piperidinyl)ethyl]-9-(2,3,5-tri-O-acetyl-β-D-ribofuranosyl)-9H-purine-2-carboxamide (assumed to be 310 g, 0.426 moles) (Preparation 24) and 1,2-dimethoxyethane (1600 ml) was added 5M aqueous sodium hydroxide solution (640 ml, 3.2 moles) over a 45 minute period with cooling in ice. The resultant mixture was stirred at ambient temperature for 3 hours, and then the layers were separated. The stirred organic phase was then diluted with deionised water (1800 ml) with cooling. When the addition was complete, the resultant mixture was heated to 50–55° C. whereupon crystallisation started. To this heated and stirred suspension was added further deionised water (1800 ml) over a period of 50 minutes. Once the addition was complete, the resultant slurry was cooled to 10° C. over a period of 45 minutes and the resulting solid was then collected by filtration. The solid was washed with a solution of 1,2-dimethoxyethane (400 ml) and deionised water (800 ml) and was then dried at 55° C. under reduced pressure to give the crude title compound as a brown solid (203 g).

This material was combined with material obtained from processes carried out under similar conditions and was purified in the following manner. To a suspension of the crude title compound (398 g, 0.661 moles) in isopropanol (7050 ml) was added deionised water (1760 ml) and the resultant mixture was stirred and warmed until a dear solution was obtained. The solution was filtered and the filtrate was then distilled under nitrogen at atmospheric pressure with periodic addition of filtered isopropanol to maintain the distillation volume. Over the course of the distillation, a total of 29100 ml of distillate was collected, and a total of 26100 ml of filtered isopropanol was added. Towards the end of the distillation, the amount of water present in the distillate was measured by Karl-Fischer analysis to be <0.5% by weight. The mixture was then allowed to cool to 40° C. over 3.5 hours with stirring during which time crystallisation occurred. The resultant slurry was stirred at ambient temperature for 12.5 hours and then cooled to 2° C. in an ice-bath over 5.5 hours. The solid was collected by filtration, and the filter cake was washed with chilled, filtered isopropanol (2×1500 ml). The filter cake was dried at 60° C. under reduced pressure to give the title compound as a pale beige-coloured solid (306 g), m.p. 182° C.

LRMS (positive atmospheric pressure chemical ionisation): m/z [MH+] 602.

¹H-NMR (500 MHz, d₆-DMSO) δ: 8.50 (1H, br t), 8.40 (1H, s), 8.00 (1H, br t), 7.35 (4H, d), 7.26 (4H, t), 7.15 (2H, t), 5.91 (1H, d), 5.39 (1H, d), 5.14 (1H, d), 5.06 (1H, t), 4.64–4.50 (2H, m), 4.28–4.18 (2H, m), 4.18–4.10 (1H, m), 3.96–3.90 (1H, m), 3.70–3.61 (1H, m), 3.60–3.50 (1H, m), 3.46–3.37 (2H, m), 2.50–2.44 (2H, m, partly obscured by DMSO peak), 2.40–2.32 (4H, m), 1.46–1.38 (4H, m), 1.36–1.28 (2H, m).

$[\alpha]_D^{25}$ (c=0.1 in methanol): −30°

The following Preparations describe the preparation of certain intermediates used in the preceding Examples.

Preparation 1

(2R,3R,4R,5R)-4-(Acetyloxy)-2-[(acetyloxy) methyl]-5-{6-[(2,2-diphenylethyl)amino]-2-iodo-9H-purin-9-yl}tetrahydro-3-furanyl acetate

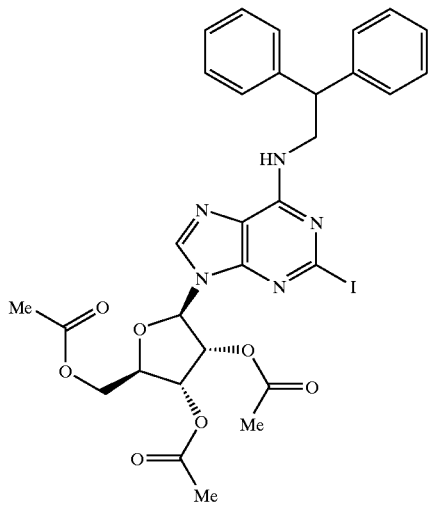

A mixture of (2R,3R,4R,5R)-4-(acetyloxy)-2-[(acetyloxy)methyl]-5-(6-chloro-2-iodo-9H-purin-9-yl) tetrahydro-3-furanyl acetate (J. Med. Chem., 35, 248, (1992)) (15.2g, 28.2 mmol), 2,2-diphenylethylamine (6.1 g, 30.9 mmol), triethylamine (11.4 g, 112.8 mmol) and acetonitrile (200 ml) was stirred at room temperature, under a nitrogen atmosphere, for 24 hours, followed by heating under reflux for 90 minutes. The solvent was removed under reduced pressure and the residue partitioned between dichloromethane (500 ml) and water (200 ml). The organic phase was separated and the solvent removed under reduced pressure to give the title compound as a pale yellow foam (18.8g).

¹H-NMR (CDCl₃) δ: 7.70 (1H, s), 7.20–7.39 (10H, m), 6.11 (1H, d), 5.75 (2H, t), 5.61 (1H, m), 4.20–4.48 (6H, m), 2.19 (3H, s), 2.13 (3H, s), 2.09 (3H, s).

Preparation 2

(2R,3R,4S,5R)-2-{6-[(2,2-Diphenylethyl)amino]-2-iodo-9H-purin-9-yl}-5-(hydroxymethyl)tetrahydro-3,4-furandiol

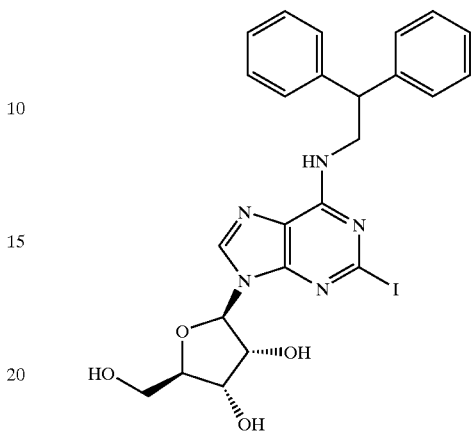

(2R,3R,4R,5R)-4-(Acetyloxy)-2-[(acetyloxy)methyl]-5-{6 [(2,2-diphenylethyl)amino]-2-iodo-9H-purin-9-yl}tetrahydro-3-furanyl acetate (1.7 g, 2.43 mmol) (Preparation 1) was dissolved in 10:1, by volume, methanol water (88 ml). Solid sodium carbonate (1.5 g, 14.1 mmol) was added and the mixture stirred at room temperature for 90 minutes before removing the methanol by evaporation under reduced pressure. The residual aqueous solution was diluted with water (50 ml) and extracted with ethyl acetate (150 ml). The organic phase was washed sequentially with water and brine, dried over anhydrous sodium sulphate and the solvent removed under reduced pressure to yield the title compound as a white solid (1.4 g).

¹H-NMR (CDCl₃) δ: 7.58 (1H, s), 7.19–7.37 (10H, m), 5.95 (1H, br d), 5.69 (1H, br d), 5.00 (1H, q), 4.50–4.62 (1H, br), 4.20–4.40 (3H, m), 3.90–4.05 (1H, m), 3.75 (1H, t).

Preparation 3

9-[(3aR,4R,6R,6aR)-6-({[tert-Butyl(dimethyl)silyl]oxy}methyl)-2,2-dimethyltetrahydrofuro[3,4-d][1,3]dioxol-4-yl]-6-chloro-2-(tributylstannyl)-9H-purine

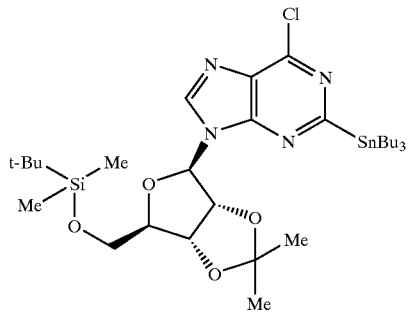

A solution of 2,2,6,6-tetramethylpiperidine (17.6 g, 125 mmol) in dry tetrahydrofuran (350 ml) was cooled to −50° C., under an atmosphere of nitrogen gas, and treated with n-butyllithium (78 ml, 1.6M solution in hexanes, 125 mmol) over 15 minutes. The reaction mixture was then cooled to −70° C. and a solution of 9-[(3aR,4R,6R,6aR)-6-({[tert-butyl(dimethyl)silyl]oxy}methyl)-2,2-dimethyltetrahydrofuro[3,4-d][1,3]dioxol-4-yl]-6-chloro- 9H-purine (Bioorg. Med. Chem. Lett., 8, 695–698, (1998)) (11.0 g, 25 mmol) in dry tetrahydrofuran (150 ml) was added, dropwise, keeping the temperature below −70° C. The reaction mixture was stirred for 30 minutes. Tri-n-butyl tin chloride (40.7 g, 125 mmol) was then added to the reaction and the mixture stirred at −70° C. for 30 minutes. A saturated solution of ammonium chloride in water (100 ml) was added to the reaction which was then warmed to 0° C. A saturated aqueous solution of sodium hydrogen carbonate was added (150 ml) and the mixture extracted with ethyl acetate (3×100 ml). The combined organic extracts were washed with brine, dried over anhydrous sodium sulphate, filtered and the solvent removed under reduced pressure. The residue was purified by column chromatography on silica gel eluting with a gradient system of hexane:ethyl acetate (95:5, by volume) gradually changing to hexane:ethyl acetate (80:20, by volume) to afford the title compound (13.0 g).

$^1$H-NMR (CDCl$_3$) δ: 8.24 (1H, s), 6.24 (1H, d), 5.35 (1H, dd), 4.93 (1H, dd), 4.42 (1H, m), 3.84 (1H, dd), 3.77 (1H, dd), 1.50–1.70 (9H, m), 1.10–1.45 (15H, m), 0.90 (9H, t), 0.84 (9H, s), 0.00 (6H, s).

LRMS (thermospray): m/z [MH$^+$] 732

Preparation 4

9-[(3aR,4R,6R,6aR)-6-({[tert-Butyl(dimethyl)silyl]oxy}methyl)-2,2-dimethyltetrahydrofuro[3,4-d][1,3]dioxol-4-yl]-N-(2,2-diphenylethyl)-2-(tributylstannyl)-9H-purin-6-amine

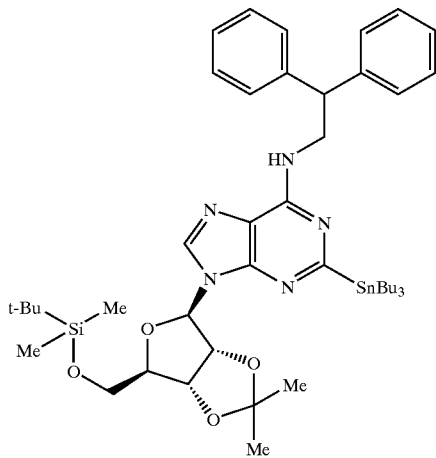

A mixture of 9-[(3aR,4R,6R,6aR)-6-({[tert-butyl(dimethyl)silyl]oxy}methyl)-2,2-dimethyltetrahydrofuro[3,4-d][1,3]dioxol-4-yl]-6-chloro-2-(tributylstannyl)-9H-purine (12.0 g, 16.4 mmol) (Preparation 3), 2,2-diphenylethylamine (3.56 g, 18.0 mmol), triethylamine (3.30 g, 33.0 mmol) and acetonitrile (50 ml) was heated at 80° C. for 18 hours. Further 2,2-diphenylethylamine (0.75 g, 3.8 mmol) was then added and the heating continued for 5 hours. The mixture was cooled, poured into water and extracted with ethyl acetate (3×50 ml). The combined organic extracts were washed with brine, dried over anhydrous sodium sulphate, filtered and the solvent removed under reduced pressure. The residue was purified by column chromatography on silica gel eluting with a gradient of hexane:ethyl acetate (4:1, by volume) gradually changing to hexane:ethyl acetate (2:1, by volume) to afford the title compound as an oil (10.3 g).

$^1$H-NMR (CDCl$_3$) δ: 7.74 (1H, s), 7.14–7.37 (10H, m), 6.10 (1H, d), 5.52–5.62 (2H, m), 5.00 (1H, dd), 4.44 (1H, t), 4.25–4.38 (3H, m), 3.78 (1H, dd), 3.72 (1H, dd), 1.48–1.78 (9H, m), 1.30–1.44 (9H, m), 1.17 (6H, t), 0.88 (9H, t), 0.82 (9H, s), −0.06 (6H, s).

LRMS (thermospray): m/z [MH$^+$] 891

Preparation 5

9-[(3aR,4R,6R,6aR)-6-({[tert-Butyl(dimethyl)silyl]oxy}methyl)-2,2-dimethyltetrahydrofuro[3,4-d][1,3]dioxol-4-yl]-N-(2,2-diphenylethyl)-2-iodo-9H-purin-6-amine

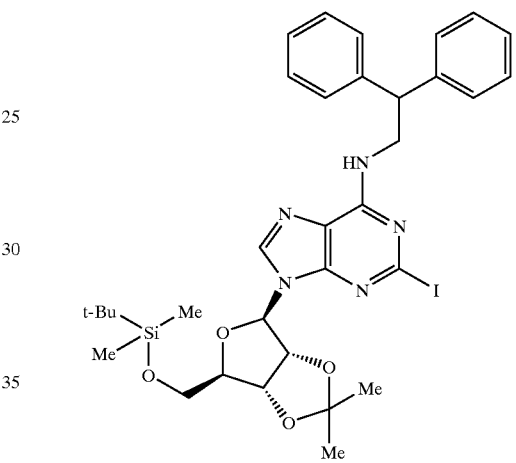

A mixture of 9-[(3aR,4R,6R,6aR)-6-({[tert-butyl(dimethyl)silyl]oxy}methyl)-2,2-dimethyltetrahydrofuro[3,4-d][1,3]dioxol-4-yl]-N-(2,2-diphenylethyl)-2-(tributylstannyl)-9H-purin-6-amine (1.0 g, 1.12 mmol) (Preparation 4), iodine (0.43 g, 1.68 mmol) and tetrahydrofuran (30 ml) was stirred at 50° C. for 30 minutes. The mixture was cooled, dissolved in ethyl acetate and washed sequentially with saturated aqueous sodium thiosulphate solution followed by water. The organic phase was separated, dried over anhydrous sodium sulphate, filtered and the solvent removed under reduced pressure. The residue was purified by column chromatography on silica gel eluting with a gradient system of hexane gradually changing to hexane:ethyl acetate (50:50, by volume) to afford the title compound (1.05 g).

$^1$H-NMR (CDCl$_3$) δ: 7.77 (1H, br s), 7.16–7.36 (10H, m), 6.06 (1H, br s), 5.72 (1H, br s), 5.20 (1H, dd), 4.96 (1H, dd), 4.15–4.42 (4H, m), 3.84 (1H, dd), 3.78 (1H, dd), 1.62 (3H, s), 1.38 (3H, s), 0.86 (9H, s), 0.02 (6H, s).

LRMS (thermospray): m/z [MH$^+$] 728

Preparation 6
9-[(3aR,4R,6R,6aR)-6-({[tert-Butyl(dimethyl)silyl[oxy}methyl)-2,2-dimethyltetrahydrofuro[3,4-d[]1,3]dioxol-4-yl]-6-[(2,2-diphenylethyl)amino]-N-phenethyl-9H-purine-2-carboxamide

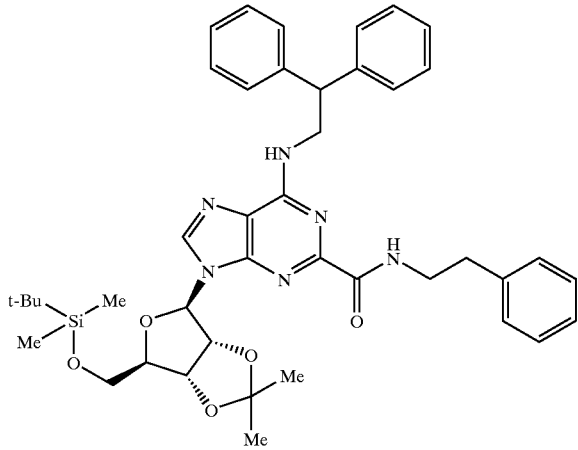

A mixture of 9-[(3aR,4R,6R,6aR)-6-({[tert-butyl(dimethyl)silyl]oxy}methyl)-2,2-dimethyltetrahydrofuro[3,4-d][1,3]dioxol-4-yl]-N-(2,2-diphenylethyl)-2-iodo-9H-purin-6-amine (1.0 g, 1.37 mmol) (Preparation 5), 1,1'-bis(diphenylphosphino)ferrocenedichloropalladium(II) (1:1 complex with dichloromethane) (0.1 g, 0.14 mmol), phenethylamine (0.5 g, 4.1 mmol) and tetrahydrofuran (30 ml) was heated at 60° C. under a carbon monoxide atmosphere at 345 kPa (50 psi) in a sealed vessel for 18 hours. The mixture was cooled and the solvent removed under reduced pressure. The residue was purified by column chromatography on silica gel eluting with a gradient system of hexane:ethyl acetate (2:1, by volume) gradually changing to hexane:ethyl acetate (1:1, by volume) to afford the title compound as a foam (0.72 g).

$^1$H-NMR (CDCl$_3$) δ: 7.90–8.10 (2H, m), 7.10–7.40 (15H, m), 6.26 (1H, d), 5.78 (1H, m), 5.14 (1H m), 4.97 (1H, m), 4.10–4.44 (4H, m), 3.88 (1H, dd), 3.82 (1H, dd), 3.73 (2H, q), 2.94 (2H, t), 1.62 (3H, s). 1.38 (3H, s), 0.84 (9H, s), 0.02 (6H, s).

LRMS (thermospray): m/z [MH$^+$] 749

Preparation 7
9-[(3aR,4R,6R,6aR)-6-(Hydroxymethyl)-2,2-dimethyltetrahydrofuro[3,4-d][1,3]dioxol-4-yl]-6-(2,2-diphenylethyl)amino]-N-phenethyl-9H-purine-2-carboxamide

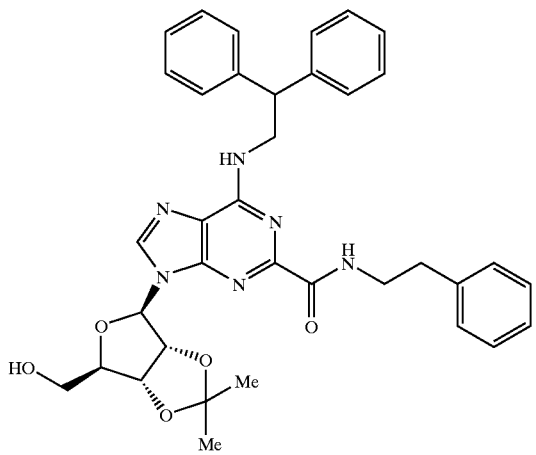

A solution of 9-[(3aR,4R,6aR)-6-({[tert-butyl(dimethyl)silyl]oxy}methyl)-2,2-dimethyltetrahydrofuro[3,4-d][1,3]dioxol-4-yl]6-[(2,2-diphenylethyl)amino]-N-phenethyl-9H-purine-2-carboxamide (0.72 g, 0.96 mmol) (Preparation 6) in acetonitrile (10 ml) was treated with tetra-n-butylammonium fluoride (1.44 ml, 1 M solution in tetrahydrofuran, 1.4 mmol) and the resulting mixture stirred at room temperature for 1 hour. The solution was then partitioned between ethyl acetate and a saturated aqueous solution of sodium hydrogen carbonate. The organic phase was separated and the aqueous phase extracted again with ethyl acetate. The combined organic phases were then washed with brine, dried over anhydrous sodium sulphate and the solvent removed under reduced pressure. The residue was purified by column chromatography on silica gel eluting with a gradient system of dichloromethane gradually changing to dichloromethane:methanol (95:5, by volume) to afford the title compound as an off-white foam (580 mg).

$^1$H-NMR (CDCl$_3$) δ: 7.92 (H, t), 7.77 (1H, s), 7.02–7.40 (15H, m), 5.94 (1H, br s), 5.70–5.85 (2H, m), 5.18–5.36 (2H, m), 4.52 (1H, s), 3.96–4.38 (4H, m), 3.58–3.92 (3H, m), 2.92 (2H, t), 1.64 (3H, s), 1.37 (3H, s).

LRMS (thermospray): m/z [MH$^+$] 1635

Preparation 8
2.6-Dichloro-(9-tetrahydro-2H-pyran-2-yl)-9H-purine

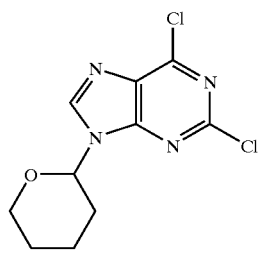

2,6-Dichloro-9H-purine (20 g, 0.11 mol) and 4-toluenesulphonic acid monohydrate (0.2 g) were dissolved in ethyl acetate (300 ml), the mixture heated to 50° C. and a solution of 2,3-dihydropyran (12.6 ml, 0.14 mol) in ethyl acetate (50 ml) added slowly over 30 minutes. The reaction mixture was cooled to room temperature, water (100 ml) added and the pH of the solution adjusted to 7 by addition of a saturated aqueous solution of sodium hydrogen carbonate. The organic layer was separated, washed sequentially with water and brine, dried over anhydrous magnesium sulphate, filtered and the solvent removed under reduced pressure. The residue was azeotroped twice with pentane to afford the slightly impure title compound as a white solid (30.9 g).

¹H-NMR (400 MHz, CDCl₃) δ: 8.30 (1H, s), 5.75 (1H, dd), 4.25–4.15 (1H, m), 3.85–3.70 (1H, m), 2.20–1.60 (6H, m).

Preparation 9

2-Chloro-N-(2,2-diphenylethyl)-(9-tetrahydro-2H-pyran-2-yl)-9H-purin-6-amine

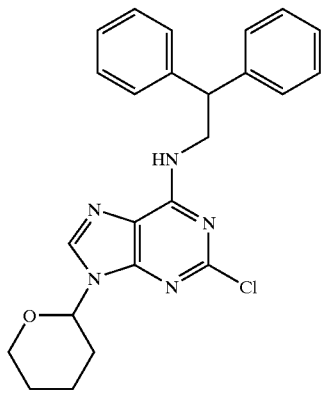

A solution of 2,6-dichloro-(9-tetrahydro-2H-pyran-2-yl)-9H-purine (Preparation 8) (30.9 g, 0.11 mol) in isopropyl alcohol (600 ml) was treated with N-ethyl-N-isopropyl-2-propanamine (47.5 ml, 0.27 mol) and 2,2-diphenylethylamine (24.8 g, 0.13 mol) and the resulting mixture heated under reflux for 3 hours. The solvent was removed under reduced pressure and the residue azeotroped with ethyl acetate. The residue was then purified by column chromatography on silica gel eluting with a gradient system of ethyl acetate:hexane (40:60, by volume) gradually changing to ethyl acetate:hexane (60:40, by volume) to afford the title compound as a foam (49.7 g).

¹H-NMR (400 MHz, CDCl₃) δ: 7.95–7.75 (1H, br s), 7.35–7.15 (10H, m), 5.80–5.70 (1H, br s), 5.65 (1H, d), 4.35 (1H, m), 4.30–4.18 (1H, br s), 4.10 (1H, d), 3.70 (1H, t), 2.05–1.95 (2H, m), 1.95–1.80 (1H, m), 1.80–1.55 (3H, m).

Preparation 10

N-(2,2-Diphenylethyl)-2-(methylsulfanyl)-9-(tetrahydro-2H-pyran-2-yl)-9H-purin-6-amine

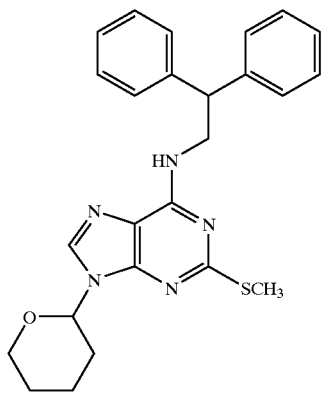

A solution of 2-chloro-N-(2,2-diphenylethyl)-9(tetrahydro-2H-pyran-2-yl)-9H-purin-6-amine (Preparation 9) (49.7 g, 0.11 mol) and dry N,N-dimethylformamide (200 ml) was treated with sodium thiomethoxide (10 g, 0.14 mol) and the resulting mixture heated under an atmosphere of nitrogen at 100° C. for 90 minutes. The mixture was stirred at room temperature for 72 hours and heated at 100° C. for a further 2 hours. The reaction mixture was cooled and diluted with water (1000 ml). A suspension was formed which was extracted with diethyl ether (2×500 ml). The combined organic layers were washed sequentially with water and brine, dried over anhydrous magnesium sulphate, filtered and the solvent removed under reduced pressure. The residue was azeotroped with diethyl ether then pentane to afford the title compound as a foam (48.9 g).

¹H-NMR (400 MHz, CDCl₃) δ: 7.80 (1H, s), 7.20–7.10 (10H, m). 5.70–5.55 (2H, d), 4.40–4.20 (3H, m), 4.20–4.05 (1H, m), 3.80–3.65 (1H, m), 2.60 (3H, s), 2.15–1.90 (3H, m), 1.90–1.60 (3H, m).

Preparation 11

N-(2,2-Diphenylethyl)₂-(methylsulfonyl 9-(tetrahydro-2H-pyran-2-yl)-9H-purin-6-amine

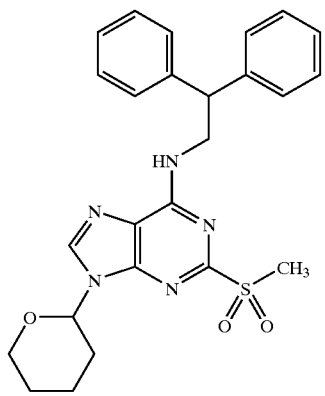

A solution of Oxone (trade mark) (potassium peroxymonosulphate) (44 g, 71.7 mmol) in water (200 ml) was added dropwise over 2 hours to a solution of N-amine (Preparation 10) (25 g 56.2 mmol), sodium hydrogen carbonate (20 g, 238 mmol), acetone (1000 ml) and water (250 ml). The resultant mixture was stirred at room temperature for 24 hours, filtered and the residue washed with acetone. The acetone was removed from the filtrate by evaporation under reduced pressure and the resulting aqueous residue was extracted with ethyl acetate and then dichloromethane. The combined organic layers were washed with brine, dried using anhydrous magnesium sulphate, filtered and the solvent removed under reduced pressure. The residue was triturated with diethyl ether, filtered, washed with diethyl ether and pentane and then dried to afford the title compound as a white solid (20.32 g).

¹H-NMR (CDCl₃)δ: 8.00 (1H, s), 7.35–7.15 (10H, m), 6.05–5.95 (1H, br s), 5.75 (1H, d), 4.40–4.35 (1H, m), 4.35–4.20 (2H, br s), 4.15–4.05 (1H, m), 3.75 (1H, t), 3.30 (3H, s), 2.18–2.05 (1H, m), 2.05–1.98 (1H, m), 1.98–1.80 (1H, m), 1.80–1.60 (3H, m).

Preparation 12

6-[(2,2-Diphenylethyl)amino]-9-tetrahydro-2H-pyran-2-yl)-9H-purine-2-carbonitrile

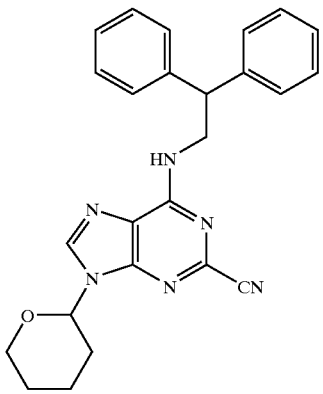

A solution of N-(2,2-diphenylethyl)-2-(methylsulfonyl)-9-(tetrahydro-2H-pyran-2-yl)-9H-purin-6-amine (Preparation 11) (20.1 g, 42.1 mmol) and dry N,N-dimethylformamide (100 ml) was treated with potassium cyanide (5.5 g, 84.6 mmol) and the mixture heated at 120° C. for 24 hours under a nitrogen atmosphere. The mixture was cooled to room temperature, poured into water (1000 ml) and stirring continued for a further 1 hour. The resultant solid was slowly filtered off and washed several times with water. The solid was dissolved in dichloromethane and the solution washed with water, dried with anhydrous magnesium sulphate, filtered and the solvent removed under reduced pressure. The residue was azeotroped with diethyl ether (twice) to afford the title compound as an oil (17 g).

$^1$H-NMR (400 MHz. CDCl$_3$) δ: 8.00 (1H, s), 7.40–7.20 (10H, m), 6.00–5.75 (1H, br s), 5.70 (1H, d), 4.40–4.20 (3H, m), 4.20–4.10 (1H, m), 3.80–3.70 (1H, m), 2.20–1.90 (3H, m), 1.90–1.60 (3H, m).

Preparation 13

6-[(2,2-Diphenylethyl)amino]-9-(tetrahydro-2H-pyran-2-yl)-9H-purine-2-carbonitrile

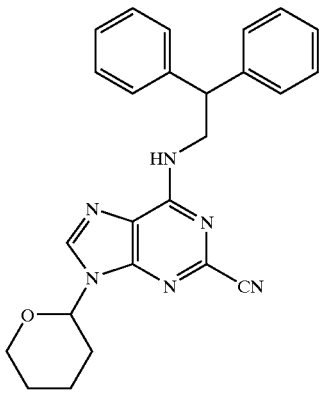

A solution of 2-chloro-N-(2,2-diphenylethyl)-9-(tetrahydro-2H-pyran-2-yl)-9H-purin-6-amine (Preparation 9) (1.0 g. 2.31 mmol), zinc cyanide (0.162 g, 1.38 mmol), triethylamine (0.28 g, 2.77 mmol), tetrakis (triphenylphosphine palladium(0) (0.133 g, 0.12 mmol) and N,N-dimethylformamide (3 ml) was heated under a nitrogen atmosphere at 100° C. for 6 hours. The reaction mixture was allowed to cool and partitioned between ethyl acetate (100 ml) and 2 M aqueous sodium hydroxide solution (100 ml). The organic layer was separated, dried over anhydrous magnesium sulfate and evaporated under reduced pressure. The resulting 1:1 mixture of 6-[(2,2-diphenylethyl)amino]-9-(tetrahydro-2H-pyran-2-yl)-9H-purine-2-carbonitrile and 6-[(2,2-diphenylethyl)amino]-9H-purine-2-carbonitrile (e.g. see Preparation 15) was separated by column chromatography on silica gel eluting with a gradient system of ethyl acetate:hexane (40:60, by volume) gradually changing to ethyl acetate:hexane (60:40, by volume) to give the title compound as a white solid (0.4 g).

$^1$H-NMR (400 MHz, CDCl$_3$) δ: 8.00 (1H, s), 7.40–7.20 (10H, m), 6.00–5.75 (1H, br s), 5.70 (1H, d), 4.40–4.20 (3H, m), 4.20–4.10 (1H, m), 3.80–3.70 (1H, m), 2.20–1.90 (3H, m), 1.90–1.60 (3H, m).

Preparation 14

Methyl 6[(2,2-phenylethyl)amino]-9-(tetrahydro-2H-pyran-2-yl)-9H-purine-2-carboxylate

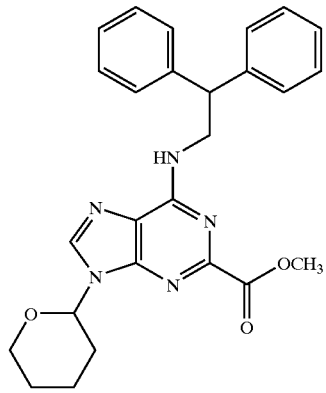

A suspension of 6-[(2,2-diphenylethyl)amino]-9 (tetrahydro-2H-pyran-2-yl)-9H-purine-2-carbonitrile (Preparation 12 or 13) (1.00 g, 2.36 mmol) in methanol (20 ml) was treated with sodium methoxide (0.14 g, 2.59 mmol) and the resulting mixture heated under reflux under a nitrogen atmosphere for 20 hours. TLC analysis showed that some starting material still remained and therefore further sodium methoxide (64 mg, 1.18 mmol) was added and mixture heated under reflux under a nitrogen atmosphere for one hour. The mixture was cooled to room temperature and the solvent removed under reduced pressure. Tetrahydrofuran (30 ml) and water (10 ml) were added to the residue and the pH adjusted to 4 by addition of glacial acetic acid (1 ml). This mixture was heated under reflux for 1 hour. TLC analysis showed that some starting material still remained and therefore further acetic acid (0.5 ml) was added and heating under reflux continued for 18 hours. The reaction mixture was cooled to room temperature and partitioned between ethyl acetate and a saturated aqueous solution of sodium hydrogen carbonate. The organic phase was separated, washed with brine, dried over anhydrous magnesium sulphate, filtered and the solvent removed under reduced pressure. The residue was purified by column chromatography on silica gel eluting with dichloromethane:methanol (98.5:1.5, by volume) to afford the title compound (521 mg).

$^1$H-NMR (400 MHz, CDCl$_3$) δ: 8.05 (1H, br s), 7.18–7.37 (10H, m), 5.84 (2H, m), 4.40 (3H, m), 4.14 (1H, d), 4.00 (3H, s), 3.78 (1H, t), 1.60–2.17 (6H, m).

LRMS (thermospray): m/z [MH⁺] 458, [MNa⁺] 480

Preparation 15

6-[(2,2-Diphenylethyl)amino]-9H-purine-2-carbonitrile

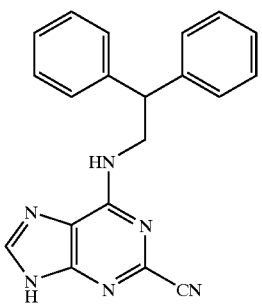

A solution of 6-[(2,2-diphenylethyl)amino]-9-(tetrahydro-2H-pyran-2-yl)-9H-purine-2-carbonitrile (Preparation 12 or 13) (17 g, 40.1 mmol) and ethanol (850 ml) was treated with 2 N aqueous hydrochloric acid solution (50 ml) and the mixture stirred at room temperature for 24 hours. The solvent was removed under reduced pressure, the residue dissolved in ethanol and the solvent again removed under reduced pressure. The residue was triturated with diethyl ether, filtered, washed with diethyl ether and pentane and dried to afford the title compound as a solid (13.6 g).

$^1$H-NMR (400 MHz, DMSO-d$_6$) δ: 8.30 (1H, s), 8.20–0.05 (1H, br s), 7.40–7.10 (10H, m), 4.60–4.40 (1.4H, m), 4.20–4.00 (1.6H, m).

LRMS (thermospray): m/z [MH⁺] 341

Preparation 16

Methyl 6-[(2,2-diphenylethyl)amino]-9H-purine-2-carboxylate

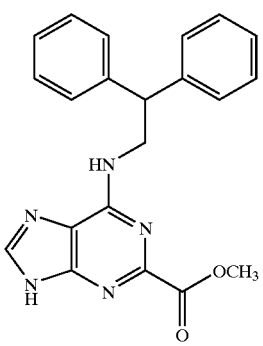

A solution of 6-[(2,2-diphenylethyl)amino]-9H-purine-2-carbonitrile (Preparation 15) (5.0 g, 14.7 mmol) and sodium methoxide (4.0 g, 74.1 mmol) in methanol (300 ml) was heated under reflux for 24 hours. Further sodium methoxide (2.0 g, 37 mmol) and methanol (100 ml) was then added and heating continued for a further 24 hours. The reaction mixture was cooled and the solvent removed under reduced pressure. The residue was dissolved in tetrahydrofuran (375 ml), 2 M aqueous hydrochloric acid solution (125 ml) added and the mixture stirred at room temperature for 24 hours. The tetrahydrofuran was removed under reduced pressure and the pH of the suspension adjusted to 7 with saturated aqueous sodium bicarbonate solution. Ethyl acetate (100 ml) was then added and the suspended white solid filtered off, washed with a little water then ethyl acetate and dried. Purification by column chromatography on silica gel eluting with a gradient system of dichloromethane:methanol (90:10, by volume) gradually changing to dichloromethane:methanol (75:25, by volume) afforded the title compound as a white solid (1.25 g) (n.b. evaporation of the ethyl acetate filtrate provided 2.6 g of the starting material).

$^1$H-NMR (400 MHz, CDCl$_3$) δ: 12.40 (1H, br s), 8.05 (1H, s), 7.55 (1H, s), 7.30–7.20 (10H, m), 4.80 (2H, m), 4.75 (1H, m), 3.80 (3H, s).

LRMS (thermospray): m/z [MH⁺] 375

Preparation 17

Methyl 9-{(2R,3R,4R,5R)-3,4-bis(acetyloxy)-5-[(acetyloxy)methyl]tetrahydro-2-furanyl}-6-[(2,2-diphenylethyl)amino]-9 H-purine-2-carboxylate

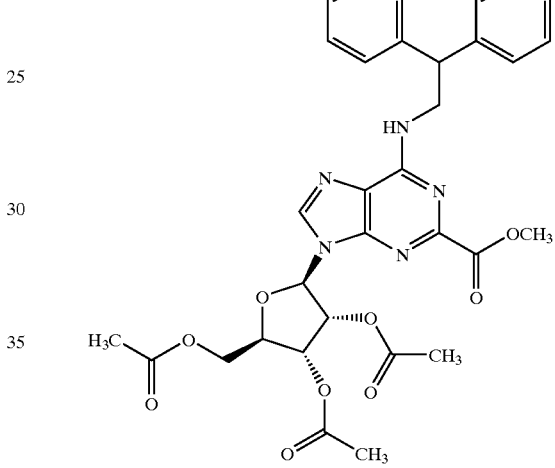

A suspension of methyl 6-[(2,2-diphenylethyl)amino]-9H-purine-2-carboxylate (Preparation 16) (1.5 g, 4.02 mmol) in 1,1,1-trichloroethane (40 ml) was treated with N,O-bis(trimethylsilyl)acetamide (4.8 ml, 19.6 mmol). The mixture was heated under reflux for two hours. The solution was allowed to cool to room temperature and the solvent removed under reduced pressure. The residue was taken up in anhydrous toluene (40 ml) and 1,2,3,5-tetra-O-acetyl-β-D-ribofuranose (1.65 g, 5.19 mmol) and trimethylsilyl trifluoromethanesulfonate (0.98 ml, 5.43 mmol) added. The resulting solution was heated under reflux under a nitrogen atmosphere for 3 hours. The mixture was cooled to room temperature, diluted with ethyl acetate (200 ml) and washed with a saturated aqueous solution of sodium hydrogen carbonate. The organic layer was separated, dried over anhydrous magnesium sulphate, filtered and the solvent removed under reduced pressure. The residue was purified by column chromatography on silica gel using gradient elution with ethyl acetate:pentane (70:30, by volume) then ethyl acetate:pentane (80:20, by volume) then ethyl acetate to afford the title compound as a foam (2.05 g).

$^1$H-NMR (400 MHz, CDCl$_3$) δ: 8.00 (1H, br s), 7.35–7.20 (11H, m), 6.25 (1H, m), 5.85–5.70 (3H, m), 4.50–4.30 (5H, m), 4.00 (3H, s), 2.15 (3H, s), 2.10 (3H, s), 2.05 (3H, s).

LRMS (thermospray): m/z [MNa⁺] 655

Preparation 18

Methyl 9-[(2R,3R,4S,5R)-3,4-dihydroxy-5-(hydroxymethyl)tetrahydro-2-furanyl]-6-[(2,2-diphenylethyl)amino]-9H-purine-2-carboxylate

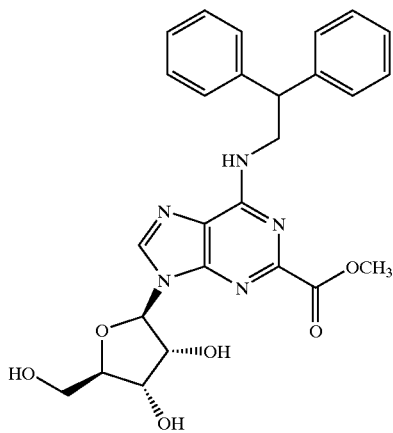

A solution of methyl 9(2R,3R,4R,5R 3,4-bis(acetyloxy)-5-[(acetyloxy)methyl]-tetrahydro-2-furanyl)-6-[(2,2-diphenylethyl)amino]-9H-purine-2-carboxylate (Preparation 17) (2.0 g, 3.17 mmol), sodium carbonate (35 mg) and dry methanol (40 ml) was stirred at room temperature for 3.5 hours. The solvent was removed under reduced pressure and the residue was purified by column chromatography on silica gel using a gradient elution with dichloromethane methanol (94:6, by volume) then dichloromethane:methanol (92:8, by volume) to afford the title compound as a white powder (1.5 g).

$^1$H-NMR (400 MHz, CDCl$_3$) δ: 7.80 (1H, br s), 7.35–7.20 (10H, m), 5.95 (1H, br s), 5.75 (2H, m), 5.10 (1H, m), 4.90 (1H, br s), 4.40 (3H, m), 4.30 (1H, s), 4.15 (1H, m), 3.90 (1H, m), 3.80–3.70 (4H, m); 3.15 (1H, s).

LRMS (thermospray): m/z [MNa$^+$] 528

Preparation 19

2-[2-(4-Isopropyl-1-piperidinyl)ethyl]-1H-isoindole-1,3(2H)-dione

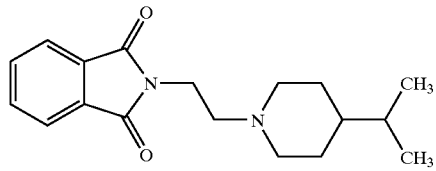

A solution of 4-isopropylpiperidine (3.3 g, 20.2 mmol), 2-bromoethylphthalimide (5.4 g, 21.3 mmol), potassium carbonate (5.9 g. 45.4 mmol) and acetonitrile (100 ml) and was heated under reflux for 2.5 hours then stirred at room temperature overnight. The solvent was removed under reduced pressure and the residue partioned between ethyl acetate (100 ml) and water (100 ml). The organic layer was separated and the aqueous layer extracted with further ethyl acetate (100 ml). The combined organic extracts were dried (Na$_2$SO$_4$) and the solvent removed by evaporation under reduced pressure. The resulting oil was purified by column chromatography on silica gel eluting with a gradient system of dichloromethane changing to dichloromethane: diethyl ether (50:50, by volume) changing to diethyl ether to afford the title compound (3.3 g).

$^1$H-NMR (400 MHz, CDCl$_3$) δ: 7.80 (2H, m), 7.70 (2H, m), 3.80 (2H, t), 3.00 (2H, m), 2.60 (2H, t), 1.95 (2H, m), 1.60 (2H, m), 1.40 (1H, m), 1.20 (2H, qd), 0.95 (1H, m), 0.80 (6H, d).

LRMS (thermospray): m/z [MH$^+$] 301

Preparation 20

2-(4-Isopropyl-1-piperidinyl)ethylamine

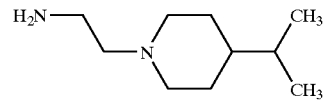

A solution of (2-[2-(4-isopropyl-1-piperidinyl)ethyl]-1H-isoindole-1,3(2H)-dione (Preparation 19) (3.2 g, 10.6 mmol) in a 33% w/w solution of methylamine in ethanol (60 ml) was heated under reflux for three hours. The solvent was removed under reduced pressure, further ethanol added (60 ml) and the solvent again removed under reduced pressure. The residue was suspended in dichloromethane (100 ml) and the solid filtered off. This was washed with dichloromethane (100 ml). The filtrate was evaporated under reduced pressure and the resulting oil purified by column chromatograpy on silica gel eluting with dichloromethane:methanol:0.88 aqueous NH$_3$ solution (90:10:1, by volume) to give a colourless oil. Bulb-to-bulb distillation (150–160° C., 30 mmHg) yielded the title compound (1.0 g, 55%).

$^1$H-NMR (400 MHz, CDCl$_3$) δ: 2.90 (2H, m), 2.80 (2H, t), 2.40 (2H, t), 1.95 (2H, m), 1.65 (2H, m), 1.40 (1H, m), 1.30–1.20 (4H, m), 1.00 (1H, m), 0.85 (6H, d).

LRMS (thermospray): m/z [MH$^+$] 171.

Preparation 21

6-[(2,2-Diphenylethyl)amino]-9-(tetrahydro-2H-pyran-2-yl)-9H-purine-2-carboxylic acid

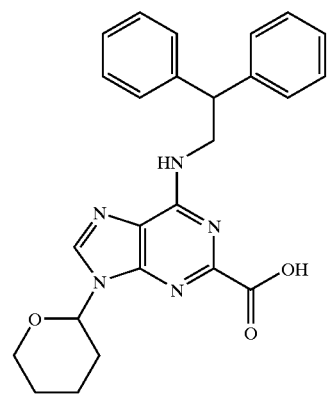

To a suspension of 6-[(2,2-diphenylethyl)amino]-9-(tetrahydro-2H-pyran-2-yl)-9H-purine-2-carbonitrile (176 g, 0.415 moles) (Preparation 13) in industrial methylated spirits (770 ml) was added a solution of sodium hydroxide (33.3 g, 0.83 moles) in deionised water (110 ml). The resultant slurry was heated under reflux for 2.5 hours during which time a clear solution formed. The mixture was allowed to cool to ambient temperature over 16 hours which resulted in the formation of a precipitate. Water (200 ml) was then added, and the mixture was distilled at atmospheric pressure. Over the course of the distillation, water (500 ml) was added periodically to the mixture, and a total of 720 ml of distillate was collected. The resultant mixture was allowed to cool slowly to ambient temperature with stirring and a thick precipitate formed. The slurry was cooled in an ice-bath, and the solid was collected by filtration. The filter cake was washed with a solution of deionised water (225 ml) and industrial methylated spirits (25 ml). The damp filter cake was suspended in a mixture of deionised water (965 ml) and dichloromethane (965 ml) and the pH of the mixture was adjusted to pH 1.2 by the addition of concentrated hydrochloric acid. The phases were separated and the aqueous layer was extracted with dichloromethane (300 ml). The organic phases were combined and the solvent was distilled at atmospheric pressure until 750 ml of distillate had collected. Ethyl acetate (1100 ml) was added and distillation was continued until a further 750 ml of distillate had collected and an off-white precipitate had formed. The resulting slurry was allowed to cool to ambient temperature and was further cooled in an ice-bath. The solid was collected by filtration and the filter cake was washed with chilled ethyl acetate (2×350 ml). The resultant solid was dried in an oven at 70° C. under reduced pressure to give the title compound as an off-white solid (163 g), m.p. 155° C. (with decomposition).

LRMS (positive atmospheric pressure chemical ionisation): m/z [MH$^+$] 444.

$^1$H-NMR (300 MHz, CDCl$_3$) δ: 8.10 (1H, s). 7.40–7.10 (10H, m), 6.30 (1H, br s), 5.90 (1H, d), 4.50–4.20 (3H, m), 4.15 (1H, br d), 3.80 (1H, br t). 2.20–1.60 (6H, m).

Preparation 22

6-[(2,2-Diphenylethyl)amino]-N-[2-(1-piperidinyl)ethyl]-9-(tetrahydro-2H-pyran-2-yl)-9H-purine-2-carboxamide

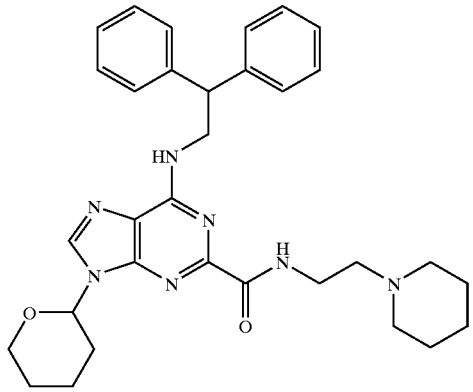

To a suspension of 6-[(2,2-diphenylethyl)amino]-9-(tetrahydro-2H-pyran-2-yl) 9H-purine-2-carboxylic acid (249 g, 0.561 moles) (Preparation 21) in anhydrous tetrahydrofuran (2500 ml) was added N,N'-carbonyldiimidazole (109 g, 0.672 moles) in two portions over 10 minutes. The resulting mixture was stirred at ambient temperature under an atmosphere of nitrogen whereupon the solid gradually dissolved to give a cloudy pale orange solution. After stirring for 2.5 h, the reaction mixture was cooled in an ice-bath, and a solution of 2-(1-piperidinyl)ethylamine (86.4 g, 0.674 moles) in anhydrous tetrahydrofuran (100 ml) was added over a period of 55 minutes during which time a clear orange solution formed. The reaction mixture was stirred at room temperature for a further 17.5 hours. Deionised water (10 ml) was then added and the reaction mixture was then distilled at atmospheric pressure until approximately 2400 ml of distillate had collected. To the resultant amber oil was added isopropanol (2000 ml) and distillation at atmospheric pressure was continued until approximately 50 ml of distillate had collected. The resultant dark orange solution was allowed to cool to ambient temperature and further isopropanol (600 ml) was added to give a solution of the title compound in isopropanol that may be used directly without further purification.

An analytical sample was prepared by the following method. A sample of the aforementioned solution of the title compound in isopropanol was concentrated under reduced pressure to an oil. The oil was dissolved in ethyl acetate and was washed successively with water and saturated aqueous sodium chloride solution. The organic phase was then dried over magnesium sulfate, and was then concentrated under reduced pressure to give the title compound as an oil. If necessary, the title compound could be purified further using preparative chromatographic methods, for example by flash chromatography.

LRMS (positive atmospheric pressure chemical ionisation): m/z [MH$^+$] 554.

$^1$H-NMR (300 MHz, CDCl$_3$) δ: 8.40 (1H, br s), 8.00 (1H, s), 7.40–7.15 (10H, m), 6.00–5.80 (2H, br d), 4.50–4.20 (3H, m), 4.10 (1H, br d), 3.80 (1H, br t), 3.55 (2H, q), 2.55 (2H, t), 2.50–2.25 (4H, m), 2.20–1.60 (6H, m), 1.60–1.25 (6H, m).

Preparation 23

6-[(2,2-Diphenylethyl)amino]-N-[2-(1-piperidinyl)ethyl]-9H-purine-2-carboxamide

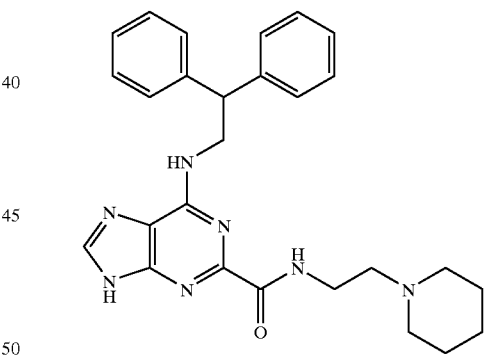

To a solution of 6-[(2,2-diphenylethyl)amino]-N-(2-(1-piperidinyl)ethyl]-9-(tetrahydro-2H-pyran-2-yl)-9H-purine-2-carboxamide (assumed to be 311 g, 0.561 moles) in isopropanol (approximately 2600 ml), obtained from Preparation 22, was added deionised water (1320 ml) over a period of 5 minutes to form a cloudy pale amber solution. To this stirred mixture was added trifluoroacetic acid (257 ml, 3.34 moles) over a period of 30 minutes so that the pH of the reaction mixture was taken below 2. The resultant mixture was then heated under reflux for 1 hour during which time a slurry was formed. The mixture was allowed to cool to ambient temperature and was stirred for 16 hours. To the stirred slurry was slowly added aqueous sodium hydroxide solution (317 ml of a 10M solution, 3.17 moles) over a period of 30 minutes until the pH of the mixture reached 11.

The pH was adjusted to pH 10 by the addition of trifluoroacetic acid (4 ml) and the resultant slurry was heated to 78° C. The mixture was cooled to ambient temperature over a period of 3 hours with stirring. The resultant slurry was filtered and the fitercake was washed with isopropanol (2×350 ml). The damp filtercake was then suspended in 1-propanol (5000 ml) and was heated under reflux during which time a solution was formed. The mixture was distilled at atmospheric pressure until 1800 ml of distillate had been collected. More 1-propanol (1800 ml) was added to the mixture and distillation was continued until 2200 ml of distillate had been collected. Distillation was stopped and the mixture was allowed to cool to ambient temperature over 16 hours with stirring during which time crystallisation occurred. The resultant slurry was cooled to 8° C. in an ice-bath and the solid was collected by filtration. The filter cake was washed with 1-propanol (1000 ml) and was then dried at 70° C. under reduced pressure to give the title compound as an off-white solid (206 g), m.p. 222° C.

LRMS (positive atmospheric pressure chemical ionisation): m/Z [MH$^+$] 470.

$^1$H-NMR (300 MHz, CDCl$_3$) δ: 15.25 (1H, br s), 8.55 (1H, br s). 8.30 (1H, s), 7.40–7.15 (10H, m), 5.90 (1H, br s), 4.50–4.25 (3H, m), 3.60 (2H, q), 2.55 (2H, t), 2.50–2.30 (4H, m), 1.50–1.20 (6H, m).

Preparation 24

6-[(2,2-Diphenylethyl)amino]-N-[2-(1-piperidinyl) ethyl]-9-(2,3,5-tri-O-acetyl-β-D-ribofuranosyl)-9H-purine-2-carboxamide

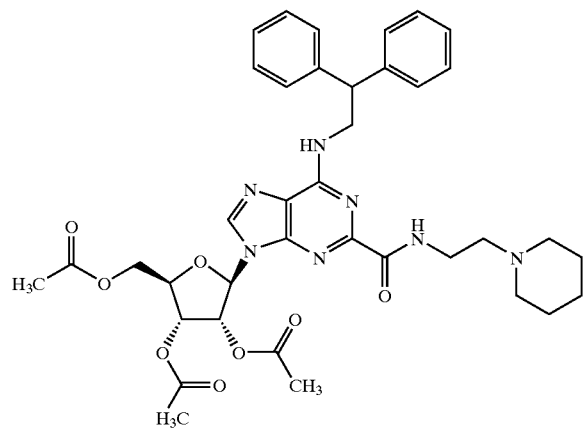

To a stirred suspension of 6-[(2,2-diphenylethyl)amino]-N-[2-(1-piperidinyl)ethyl]-9H-purine-2-carboxamide (200 g, 0.426 moles) (Preparation 23) in anhydrous 1,2-dimethoxyethane (800 ml) under an atmosphere of nitrogen was added a solution of trimethylsilyl trifluoromethanesulfonate (200 g, 0.900 moles) in anhydrous 1,2-dimethoxyethane (200 ml) over a period of 15 minutes. During the addition, all the solid dissolved to give a deep red/amber solution and the reaction temperature rose from 20° C. to 31.5° C. The resultant mixture was heated to 55–60° C. and a solution of 1,2,3,5-tetra-O-acetyl-β-D-ribofuranose (163 g, 0.512 moles) in anhydrous 1,2-dimethoxyethane (400 ml) was added over a period of 40 minutes. The addition apparatus was rinsed through into the reaction mixture with anhydrous 1,2-dimethoxyethane (200 ml). The reaction mixture was heated at 60° C. for 3 hours and was allowed to cool to ambient temperature. This crude reaction solution was held at ambient temperature for 18 hours. The resulting mixture containing the title compound may be used directly without further purification.

An analytical sample was obtained in the following manner. A sample of the aforementioned solution was added to saturated aqueous sodium bicarbonate solution and the mixture was extracted with ethyl acetate. The organic phase was washed with saturated aqueous sodium chloride solution, dried over sodium sulfate, and the solvent was then removed under reduced pressure to give a light brown foam. The crude product was purified further using preparative chromatographic methods, for example by flash chromatography on silica gel using a gradient of 5:95 changing to 15:85, by volume, methanol:dichloromethane as the mobile phase, to give the title compound as a colourless foam.

LRMS (positive atmospheric pressure chemical ionisation): m/z [MH$^+$] 728.

$^1$H-NMR (300 MHz, CDCl$_3$) δ: 8.35 (1H, br s), 7.95 (1H, s), 7.40–7.15 (10H, m), 6.35 (1H, br s), 5.90–5.70 (2H, m), 5.70–5.55 (1H, m), 4.55–4.20 (6H, m), 3.55 (2H, q), 2.55 (2H, t), 2.50–2.30 (4H, m), 2.15 (3H, s), 2.05 (6H, br s), 1.60–1.20 (6H, m).

Preparation 25

6-[(2,2-diphenylethyl)amino]-9H-purine-2-carboxylic acid

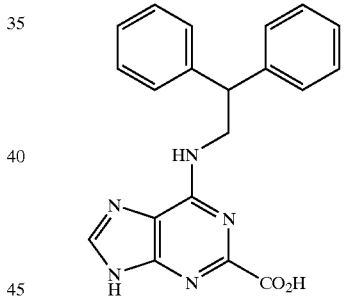

To a suspension of 6-[(2,2-diphenylethyl)amino]-9H-purine-2-carbonitrile (12.5 g, 0.0368 moles) (Preparation 15) in a mixture of industrial methylated spirits (80 ml) and deionised water (35 ml) was added sodium hydroxide (1.2 g, 0.13 moles) and the resultant mixture was heated under reflux for 17 hours during which time a clear solution was formed. The mixture was cooled to ambient temperature and was acidified by the addition of 1 M aqueous hydrochloric acid solution (105 ml) to give a suspension. The solid was collected by filtration and was dried under reduced pressure at 50° C. to give the title compound as a colourless solid (13.5 g), m.p. 241–249° C.

LRMS (negative atmospheric pressure chemical ionisation): m/z [M-H] 358.

$^1$H-NMR (300 MHz, d$_6$-DMSO) δ: 8.20 (1H, br s), 7.75 (1H, br t), 7.40–7.00 (10H, m), 4.65–4.40 (1H, m), 4.25–4.05 (2H, m).

Preparation 26

6-[(2,2-Diphenylethyl)amino]-N-[2-(1-piperidinyl)ethyl-9H-purine-2-carboxamide

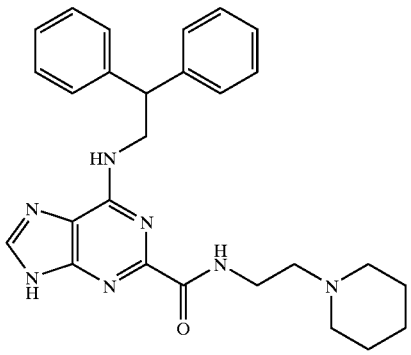

To a suspension of 6-[(2,2-diphenylethyl)amino]-9H-purine-2-carboxylic acid (0.52 g, 1.45 mmol) (Preparation 25) in N,N-dimethylformamide (20 ml) was added N,N'-carbonyldiimidazole (0.24 g, 1.48 mmol) and the resultant mixture was stirred at ambient temperature for 5 hours. To this mixture was added 2-(1-piperidinyl)ethylamine (0.206 ml, 1.45 mmol) and the resultant mixture was stirred at ambient temperature for 20 hours. The reaction mixture was filtered and the filtrate was concentrated under reduced pressure to give an oil that was partitioned between ethyl acetate (30 ml) and saturated aqueous sodium bicarbonate solution (20 ml). The layers were then separated and the aqueous phase was extracted with ethyl acetate (30 ml). The combined organic phases were then washed successively with saturated aqueous sodium bicarbonate solution (30 ml) and saturated aqueous sodium chloride solution (30 ml) and then dried (MgSO$_4$). The solvent was removed under reduced pressure to give the title compound as a brown solid (0.10 g). If required, purification of this material can be accomplished by recrystallisation from 1-propanol.

LRMS (positive atmospheric pressure chemical ionisation): m/z [MH] 470.

$^1$H-NMR (300 MHz. CDCl$_3$) δ: 15.25 (1H, br s), 8.55 (1H, br s), 8.30 (1H, s), 7.40–7.15 (10H, m), 5.90 (1H, br s), 4.50–4.25 (3H, m), 3.60 (2H, q), 2.55 (2H, t), 2.50–2.30 (4H, m), 1.50–1.20 (6H, m).

Preparation 27

Ethyl 6-[(2,2-diphenylethyl)amino]-9-(tetrahydro-2H-pyran-2-yl)-9H-purine-2-carboxylate

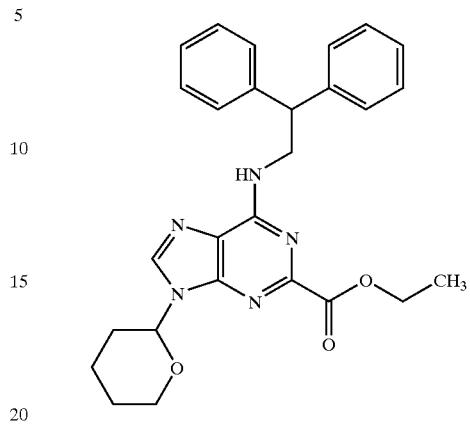

A mixture of 2-chloro-N-(2,2-diphenylethyl)-9-(tetrahydro-2H-pyran-2-yl)-9H-purin-6-amine (10 g, 23 mmol) (Preparation 9), triethylamine (9.6 ml, 69 mmol), palladium (II) acetate (0.0103 g, 0.046 mmol) and 1,1'-bis(diphenylphosphino)ferrocene (0.376 g, 0.69 mmol) in ethanol (46 ml) was heated at 120° C. under an atmosphere of carbon monoxide at 1725 kPa (250 psi) for 18 hours. The resulting slurry was cooled in an ice-bath for 2 hours and the solid was collected by filtration and washed with ethanol (20 ml). This material was then dried under reduced pressure to give an off-white solid (9.5 g). A portion of this solid (8.5 g) was suspended in ethyl acetate (170 ml) and the resultant mixture was stirred at ambient temperature for 60 hours. The mixture was filtered and the filter cake was rinsed with ethyl acetate (20 ml). The filtrate was then concentrated under reduced pressure to give the title compound as a tan coloured solid (6.45 g). A portion of this material (0.7 g) was crystallised from ethanol (3 ml) to give the title compound as a colourless solid (0.54 g), m.p. 138–140° C.

$^1$H-NMR (300 MHz, CDCl$_3$) δ: 8.05 (1H, s), 7.45–7.15 (10H, m), 5.95–5.80 (2H, m), 4.60–4.30 (5H, m), 4.15 (1H, br d), 3.80 (1H, br t), 2.20–1.60 (6H, m), 1.50 (3H, t).

LRMS (positive atmospheric pressure chemical ionisation): m/z [MH$^+$]: 472.

Preparation 28

6-[(2,2-Diphenylethyl)amino]-9-(tetrahydro-2H-pyran-2-yl)-9H-purine-2-carboxylic acid

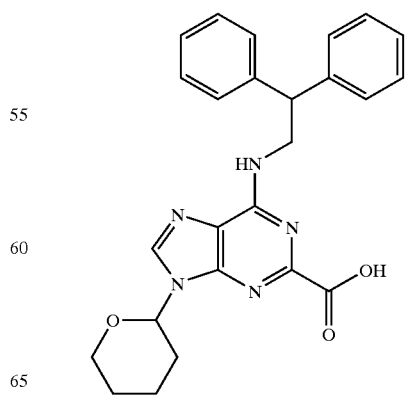

To a suspension of ethyl 6-[(2,2-diphenylethyl)amino]-9-(tetrahydro-2H-pyran-2-yl)-9H-purine-2-carboxylate (0.55 g, 1.16 mmol) (Preparation 27) in industrial methylated spirits (2.2 ml) was added deionised water (0.08 ml) followed by 10 M aqueous sodium hydroxide solution (0.23 ml, 2.3 mmol). The resultant mixture was stirred at 65° C. for 30 minutes and then at ambient temperature for 18 hours during which time a thick paste was formed. To this mixture was added dichloromethane (10 ml) and the pH was adjusted to 2 by the addition of dilute aqueous hydrochloric acid solution. The phases were separated and the aqueous layer was extracted with dichloromethane (10 ml). The combined organic phases were then dried ($MgSO_4$) and the solvent was removed under reduced pressure to give the title compound as a tan coloured foam (0.43 g) that was identical by $^1$H-NMR, high performance liquid chromatography, mass spectrometry and thin-layer chromatography to the compound prepared in Preparation 21.

Preparation 29

6-[(2,2-Diphenylethyl)amino]-9-(tetrahydro-2H-pyran-2-yl)-9H-purine-2-carboxylic acid

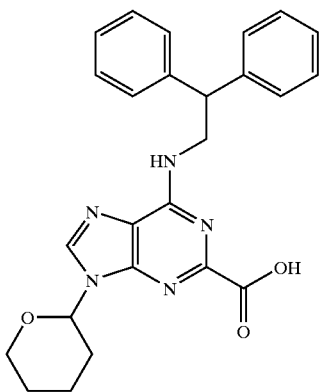

A mixture of 2-chloro-N-(2,2-diphenylethyl)-9-(tetrahydro-2H-pyran-2-yl)-9H-purin-6-amine (0.87 g, 2 mmol) (Preparation 9), palladium (II) acetate (0.002 g, 0.009 mmol), 1,1'-bis(diphenylphosphino)ferrocene (0.033 g, 0.06 mmol), 10 M aqueous sodium hydroxide solution (0.6 ml, 6 mmol) and tetrahydrofuran (4 ml) was heated at 140° C. under an atmosphere of carbon monoxide at 1725 kPa (250 psi) for 12 hours. The mixture was allowed to cool and to stand at ambient temperature for 16 days during which time a suspension formed. The solid was collected by filtration and washed with tetrahydrofuran (10 ml). This material was added to a mixture of dichloromethane (35 ml) and water (25 ml) and the pH of the mixture was adjusted to 1 by the addition of dilute aqueous hydrochloric acid solution with stirring. The layers were separated and the aqueous phase was extracted with dichloromethane (25 ml). The combined organic phases were dried ($MgSO_4$) and the solvent was removed under reduced pressure to give a the title compound as an amber foam (0.45 g) that was identical by $^1$H-NMR, high performance liquid chromatography, mass spectrometry and thin-layer chromatography to the compound prepared in Preparation 21.

Pharmacological Activity

The compounds of the preceding examples were tested for anti-inflammatory activity by their ability to inhibit neutrophil function (which indicates A2a receptor agonist activity) by the method described on page 26 and all had an $IC_{50}$ of less than 1 micromolar.

What is claimed is:
1. A compound of the formula:

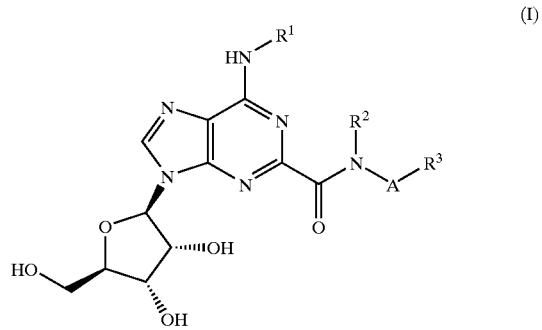

(I)

or a pharmaceutically acceptable salt or solvate thereof,
wherein $R^1$ is hydrogen or $C_1$–$C_6$ alkyl optionally substituted by 1 or 2 substituents each independently selected from phenyl and naphthyl, said phenyl and naphthyl being optionally substituted by $C_1$–$C_6$ alkyl, $C_1$–$C_6$ alkoxy, halo or cyano;

$R^2$ is H or $C_1$–$C_6$ alkyl;

A is $C_1$–$C_6$ alkylene;

$R^3$ is (i) hydrogen, $C_1$–$C_6$ alkyl, —$COOR^4$, —CN, —$CONR^4R^4$, $C_3$–$C_8$ cycloalkyl, phenyl or naphthyl, said $C_3$–$C_8$ cycloalkyl, phenyl and naphthyl being optionally substituted by $C_1$–$C_6$ alkyl, phenyl, $C_1$–$C_6$ alkoxy($C_1$–$C_6$)alkyl, $R^4R^4N(C_1$–$C_6)$alkyl, halo($C_1$–$C_6$)alkyl, fluoro($C_1$–$C_6$)alkoxy, $C_2$–$C_5$ alkanoyl, halo, —$OR^4$, cyano, —$COOR^4$, $C_3$–$C_8$ cycloalkyl, —$S(O)_mR^5$, —$NR^4R^4$, —$SO_2NR^4R^4$, —$CONR^4R^4$, —$NR^4COR^5$ or —$NR^4SO_2R^5$, or (ii) when A is $C_2$–$C_6$ alkylene, $R^3$ is —$NR^4R^4$, —$OR^4$, —$OCOR^5$, —$SO_2R^5$, —$SO_2NR^4R^4$, or —$NR^4COR^5$, or (iii) a C-linked, 4- to 11-membered ring, mono or bicyclic, heterocycle having either from 1 to 4 ring nitrogen atom(s), or 1 or 2 nitrogen and 1 oxygen or 1 sulphur ring atoms, being optionally C-substituted by oxo, $C_1$–$C_8$ alkoxy($C_1$–$C_6$)alkyl, $R^6R^6N(C_1$–$C_6)$alkyl, halo($C_1$–$C_6$)alkyl, fluoro($C_1$–$C_6$)alkoxy, fluoro($C_2$–$C_5$) alkanoyl, halo, cyano, —$OR^6$, $R^7$, —$COR^6$, —$NR^6R^6$, —$COOR^6$, —$S(O)_mR^7$, —$SO_2NR^6R^6$, —$CONR^6R^6$, —$NR^6SO_2R^7$ or —$NR^6COR^7$ and optionally N-substituted by $C_1$–$C_6$ alkoxy($C_1$–$C_6$)alkyl, $R^6R^6N$ ($C_2$–$C_6$)alkyl, halo($C_1$–$C_6$)alkyl, fluoro($C_2$–$C_5$) alkanoyl, $R^7$, —$COR^6$, —$COOR^7$, —$SO_2R^7$, —$SO_2NR^6R^6$ or —$CONR^6R^6$, or (iv) when A is $C_2$–$C_6$ alkylene, $R^3$ is an N-linked azetidinyl, pyrrolidinyl, piperidinyl, piperazinyl, homopiperazinyl or morpholinyl, each being optionally C-substituted by $C_1$–$C_6$ alkyl, phenyl, $C_1$–$C_6$ alkoxy ($C_1$–$C_6$)alkyl, $R^4R^4N(C_1$–$C_6)$alkyl, halo($C_1$–$C_6$)alkyl, fluoro($C_1$–$C_6$)alkoxy, $C_2$–$C_5$ alkanoyl, halo, —$OR^4$, cyano, —$COOR^4$, $C_3$–$C_8$ cycloalkyl, —$S(O)_mR^5$, —$NR^4R^4$, —$SO_2NR^4R^4$, —$CONR^4R^4$, —$NR^4COR^5$ or —$NR^4SO_2R^5$, and said piperazinyl and homopiperazinyl being optionally N-substituted by $C_1$–$C_6$ alkyl, phenyl, $C_1$–$C_6$ alkoxy($C_2$–$C_6$)alkyl, $R^4R^4N(C_2$–$C_6)$ alkyl, fluoro($C_1$–$C_6$)alkyl, $C_2$–$C_5$ alkanoyl, —$COOR^5$, $C_3$–$C_8$ cycloalkyl, —$SO_2R^5$, —$SO_2NR^4R^4$ or —$CONR^4R^4$;

51

$R^4$ is H, $C_1$–$C_6$ alkyl, $C_3$–$C_8$ cycloalkyl or phenyl;

$R^5$ is $C_1$–$C_5$ alkyl, $C_3$–$C_8$ cycloalkyl or phenyl;

$R^6$ is H, $C_1$–$C_6$ alkyl, $C_3$–$C_8$ cycloalkyl, phenyl, naphthyl or het;

$R^7$ is $C_1$–$C_6$ alkyl, $C_3$–$C_8$ cycloalkyl, phenyl, naphthyl or het;

m is 0, 1 or 2; and

"het", used in the definitions of $R^6$ and $R^7$, means C-linked pyrrolyl, imidazolyl, triazolyl, thienyl, furyl, thiazolyl, oxazolyl, thiadiazolyl, oxadiazolyl, pyridinyl, pyrimidinyl, pyridazinyl, pyrazinyl, indolyl, isoindolyl, quinolinyl, isoquinolinyl, benzimidazolyl, quinazolinyl, phthalazinyl, benzoxazolyl or quinoxalinyl, each being optionally substituted by $C_1$–$C_6$ alkyl, $C_1$–$C_6$ alkoxy, cyano or halo.

2. A compound as claimed in claim 1 wherein $R^1$ is $C_1$–$C_6$alkyl optionally substituted by 1 or 2 phenyl substituents.

3. A compound as claimed in claim 2 wherein $R^1$ is 2,2-diphenylethyl.

4. A compound as claimed in claim 1 wherein $R^2$ is H.

5. A compound as claimed in claim 1 wherein A is $C_1$–$C_4$ alkylene.

6. A compound as claimed in claim 5 wherein A is methylene, 1,2-ethylene or 1,3-propylene.

7. A compound as claimed in claim 6 wherein A is 1,2-ethylene.

8. A compound as claimed in claim 1 wherein $R^3$ is phenyl optionally substituted by $C_1$–$C_6$ alkyl, phenyl, $C_1$–$C_6$ alkoxy ($C_1$–$C_6$)alkyl, $R^4R^4N(C_1$–$C_6)$alkyl, halo($C_1$–$C_6$)alkyl, fluoro($C_1$–$C_6$)alkoxy, $C_2$–$C_5$ alkanoyl, halo, —$OR^4$, cyano, —$COOR^4$, $C_3$–$C_8$ cycloalkyl, —$S(O)_mR^5$, —$NR^4R^4$, —$SO_2NR^4R^4$, —$CONR^4R^4$, —$NR^4COR^5$ or —$NR^4SO_2R^5$; or, when A is $C_2$–$C_6$ alkylene, $R^3$ is —$NR^4R^4$ wherein $R^4$ is H, $C_1$–$C_6$ alkyl, $C_3$–$C_6$ cycloalkyl or phenyl; or $R^3$ is a C-linked, 5- to 7-membered ring monocyclic heterocycle having either from 1 to 4 ring nitrogen atom(s) or 1 or 2 nitrogen and 1 oxygen or 1 sulphur ring atoms, optionally C-substituted by oxo, $C_1$–$C_6$ alkoxy($C_1$–$C_6$)alkyl, $R^5R^6N$ ($C_1$–$C_6$)alkyl, halo($C_1$–$C_6$)alkyl, fluoro($C_1$–$C_6$)alkoxy, fluoro($C_2$–$C_5$)alkanoyl, halo, cyano, $OR^6$, $R^7$, $COR^6$, —$NR^6R^6$, —$COOR^6$, —$S(O)_mR^7$, —$SO_2NR^6R^6$, —$CONR^6R^6$, —$NR^6SO_2R^7$ or —$NR^6COR^7$ and optionally N-substituted by $C_1$–$C_6$ alkoxy($C_1$–$C_6$)alkyl, $R^6R^6N$ ($C_2$–$C_6$)alkyl, halo($C_1$–$C_6$)alkyl, fluoro($C_2$–$C_5$)alkanoyl, $R^7$, —$COR^6$, —$COOR^7$, —$SO_2R^7$, —$SO_2NR^6R^6$ or $CONR^6R^6$ or, when A is $C_2$–$C_6$ alkylene, $R^3$ is N-linked pyrrolidinyl, piperidinyl or morpholinyl, each being optionally C-substituted by $C_1$–$C_6$ alkyl, phenyl, $C_1$–$C_6$ alkoxy ($C_1$–$C_6$)alkyl, $R^4R^4N(C_1$–$C_6)$alkyl, halo($C_1$–$C_6$)alkyl, fluoro($C_1$–$C_6$)alkoxy, $C_2$–$C_5$ alkanoyl, halo, —$OR^4$, cyano, —$COOR^4$, $C_3$–$C_8$ cycloalkyl, —$S(O)_mR^5$, —$NR^4R^4$, —$SO_2NR^4R^4$, —$CONR^4R^4$, —$NR^4COR^5$ or —$NR^4SO_2R^5$.

9. A compound as claimed in claim 8 wherein $R^3$ is phenyl; or, when A is $C_2$–$C_6$ alkylene, $R^3$ is —$NR^4R^4$ wherein $R^4$ is $C_1$–$C_6$ alkyl; or, $R^3$ is a C-linked, 5- or 6-membered ring monocyclic aromatic heterocycle having from 1 to 4 ring nitrogen atom(s), optionally C-substituted by oxo, $C_1$–$C_6$ alkoxy($C_1$–$C_6$)alkyl, $R^6R^6N(C_1$–$C_6)$alkyl, halo($C_1$–$C_6$)alkyl, fluoro($C_1$–$C_6$)alkoxy, fluoro($C_2$–$C_5$) alkanoyl, halo, cyano, —$OR^6$, $R^7$, —$COR^6$, —$NR^6R^6$, —$COOR^6$, —$S(O)_mR^7$, —$SO_2NR^6R^6$, —$CONR^6R^6$, —$NR^6SO_2R^7$ or —$NR^6COR^7$ and optionally N-substituted by $C_1$–$C_6$ alkoxy($C_1$–$C_6$)alkyl, $R^5R^6N(C_2$–$C_6)$alkyl, halo ($C_1$–$C_6$)alkyl, fluoro($C_2$–$C_5$)alkanoyl, $R^7$, —$COR^6$, —$COOR^7$, —$SO_2R^7$, —$SO_2NR^6R^6$ or —$CONR^6R^6$; or,

52 when A is $C_2$–$C_6$ alkylene, $R^3$ is N-linked pyrrolidinyl, piperidinyl or morpholinyl, each being optionally C-substituted by $C_1$–$C_6$ alkyl or —$OR^4$ wherein $R^4$ is H, $C_1$–$C_6$ alkyl, $C_3$–$C_6$ cycloalkyl or phenyl.

10. A compound as claimed in claim 9 wherein $R^3$ is phenyl; or, when A is $C_2$–$C_6$ alkylene, $R^3$ is —$N(CH_3)_2$; or $R^3$ is C-linked pyridinyl optionally substituted by —$OR^6$, $R^7$, $C_1$–$C_6$ alkoxy($C_1$–$C_6$)alkyl, $R^6R^6N(C_1$–$C_6)$alkyl or —$NR^6R^6$ wherein $R^6$ is H, $C_1$–$C_6$ alkyl, $C_3$–$C_8$ cycloalkyl, phenyl, naphthyl or het and $R^7$ is $C_1$–$C_6$ alkyl, $C_3$–$C_8$ cycloalkyl, phenyl, naphthyl or het; or when A is $C_2$–$C_6$ alkylene, $R^3$ is pyrrolidin-1-yl, piperidin-1-yl, 4-isopropylpiperidin-1-yl or morpholin-4-yl.

11. A compound as claimed in claim 10 wherein $R^3$ is phenyl; or, when A is $C_2$–$C_6$ alkylene, $R^3$ is —$N(CH_3)_2$; or $R^3$ is 2-pyridinyl; or when A is $C_2$–$C_6$ alkylene, $R^3$ is pyrrolidin-1-yl, piperidin-1-yl, 4-isopropylpiperidin-1-yl or morpholin-4-yl.

12. A compound as claimed in claim 11 wherein, when A is $C_2$–$C_6$ alkylene, $R^3$ is piperidin-1-yl.

13. A compound as claimed in claim 1 wherein —A—$R^3$ is phenethyl, 2-(dimethylamino)ethyl, 2-pyridinylmethyl, 2-(2-pyridinyl)ethyl, 3-(1-pyrrolidinyl)propyl, 2-(1-piperidinyl)ethyl, 2-(4-isopropyl-1-piperidinyl)ethyl or 2-(4-morpholinyl)ethyl.

14. A compound as claimed in claim 13 wherein —A—$R^3$ is 2-(1-piperidinyl)ethyl.

15. A compound as claimed in claim 1 which is selected from the group consisting of 9-[(2R,3R,4S,5R)-3,4-dihydroxy-5-(hydroxymethyl) tetrahydro-2-furanyl]6-[(2,2-diphenylethyl)amino]-N-[2-(1-piperidinyl)ethyl]-9H-purine-2-carboxamide;

9-[(2R,3R,4S,5R)-3,4-dihydroxy-5-(hydroxymethyl) tetrahydro-2-furanyl]-6-[(2,2-diphenylethyl)amino]-N-phenethyl-9H-purine-2-carboxamide;

9-[(2R,3R,4S,5R)-3,4-dihydroxy-5-(hydroxymethyl) tetrahydro-2-furanyl]-6-(2,2-diphenylethyl)amino]-N-[2(4-isopropyl-1-piperidinyl)ethyl]-9H-purine-2-carboxamide;

9-[(2R,3R,4S,5R)-3,4-dihydroxy-5-(hydroxymethyl) tetrahydro-2-furanyl]-6-[(2,2-diphenylethyl)amino]-N-[3-(1-pyrrolidinyl)propyl]-9H-purine-2-carboxamide;

9-[(2R,3R,4S,5R)-3,4-dihydroxy-5 hydroxylmethyl) tetrahydro-2-furanyl]-6-[(2,2-diphenylethyl)amino]-N-[2-(4-morpholinyl)ethyl]-9H-purine-2-carboxamide;

9-[(2R,3R,4S,5R)-3,4-dihydroxy-5-(hydroxymethyl) tetrahydro-2-furanyl]-6-[(2,2-diphenylethyl)amino]-N (2-pyridinylmethyl)-9H-purine-2-carboxamide;

9-[(2R,3R,4S,5R)-3,4-dihydroxy-5-(hydroxymethyl) tetrahydro-2-furanyl]-6-[(2,2-diphenylethyl)amino]-N-[2-(2-pyridinyl)ethyl]-9H-purine-2-carboxamide; and 9-[(2R,3R,4S,5R)-3,4-dihydroxy-5-(hydroxymethyl tetrahydro-2-furanyl]-N-[2-(dimethylamino)ethyl]-6-[(2,2-diphenylethyl)amino]-9H-purine-2-carboxamide:

and the pharmaceutically acceptable salts and solvates thereof.

16. A compound as claimed in claim 1 which is 9-[(2R, 3R,4S,5R)-3,4-dihydroxy-5-(hydroxymethyl)tetrahydro-2-furanyl]-6-[(2,2-diphenylethyl)amino]-N-[2-(1-piperidinyl) ethyl]-9H-purine-2-carboxamide, or a pharmaceutically acceptable salt or solvate thereof.

17. A compound as claimed in claim 1 wherein $R^1$ is hydrogen or $C_1$-$C_6$ alkyl substituted by 1 or 2 substituents each independently selected from phenyl and naphthyl;

$R^2$ is hydrogen or $C_1$-$C_6$ alkyl;

A is $C_1$-$C_6$ alkylene; and $R^3$ is phenyl, naphthyl, $C_3$-$C_8$ cycloalkyl, azetidinyl, pyrrolidinyl, piperidinyl, amino, —NH($C_1$-$C_6$ alkyl) or —N($C_1$-$C_6$ alkyl)$_2$, said phenyl, naphthyl, $C_3$-$C_8$ cycloalkyl, azetidinyl, pyrrolidinyl and piperidinyl being optionally substituted by one or more substituents each independently selected from $C_1$-$C_6$ alkyl, $C_1$-$C_6$ alkoxy, halo($C_1$-$C_6$)alkyl, halo and cyano:

with the proviso that when $R^3$ is N-linked, optionally substituted-azetidinyl, -pyrrolidinyl or -piperidinyl, or is amino, —NH($C_1$-$C_6$ alkyl) or —N($C_1$-$C_8$ alkyl)$_2$, A is $C_2$-$C_8$ alkylene.

18. A pharmaceutical composition comprising a compound of claim 1 or a pharmaceutically acceptable salt thereof together with a pharmaceutically acceptable excipient, diluent or carrier.

19. A process for the preparation of a compound of the formula (I), or a pharmaceutically acceptable salt thereof, as claimed in claim 1 comprising a) aminocarbonylation reaction of a compound of the formula:

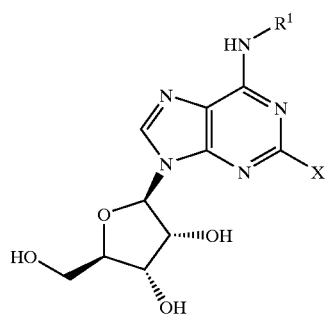

(II)

wherein $R^1$ is defined in claim 1 and X is a leaving group such as bromo, iodo, —Sn($C_1$-$C_{12}$ alkyl)$_3$ or $CF_3SO_2O$—, with a compound of the formula:

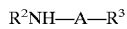

$R^2NH$—A—$R^3$    (III)

wherein A, $R^2$ and $R^3$ are as defined in claim 1, in the presence of carbon monoxide and a suitable coupling catalyst; or b) deprotection of a compound of the formula:

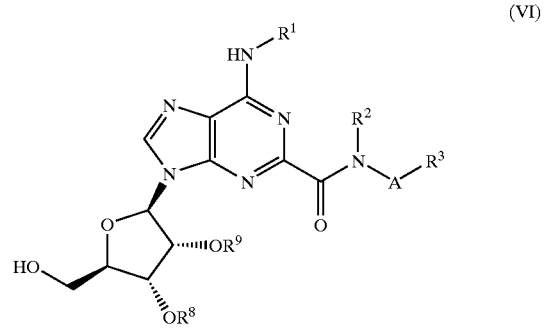

(VI)

wherein A, $R^1$, $R^2$ and $R^3$ are as defined in claim 1 and $R^8$ and $R^9$, when taken separately, are protecting groups, or, when taken together, are a protecting group; or c) deprotection of a compound of the formula:

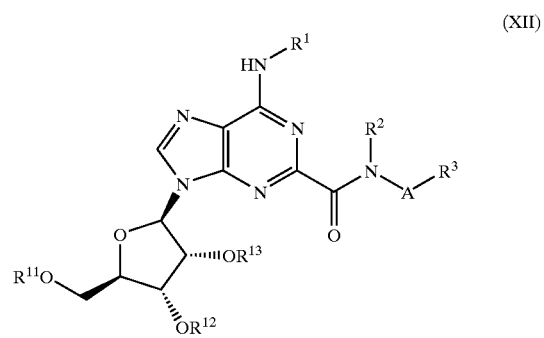

(XII)

wherein A, R1, $R^2$ and $R^3$ are as defined in claim 1 and $R^{11}$, $R^{12}$ and $R^{13}$, taken separately, are protecting groups, or $R^{11}$ is a protecting group and $R^{12}$ and $R^{13}$, taken together, are a protecting group: or d) reaction of a compound of the formula:

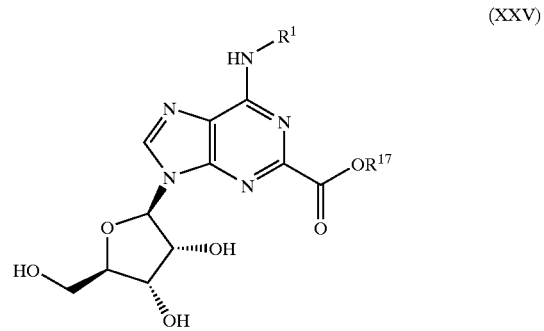

(XXV)

wherein $R^1$ is as defined in claim 1 and $R^{17}$ is H or an ester-forming group, with a compound of the formula (III) as defined in part (a), and, where $R^{17}$ is H, in the presence of a peptide coupling agent:

any one of said processes being optionally followed by conversion to a pharmaceutically acceptable salt thereof.

* * * * *